United States Patent [19]
Rhoads et al.

[11] Patent Number: 5,604,582
[45] Date of Patent: Feb. 18, 1997

[54] METHODS AND APPARATUS FOR TAKING SPECTROSCOPIC MEASUREMENTS OF SEDIMENT LAYERS BENEATH A BODY OF WATER

[75] Inventors: Donald C. Rhoads, Falmouth, Mass.; Christopher Coyle, San Diego, Calif.; Roger Ward, Portmouth, R.I.; Gregory Mooradian, Del Mar; Richard Anderson, San Diego, both of Calif.

[73] Assignee: Science Application International Corporation, San Diego, Calif.

[21] Appl. No.: 395,515

[22] Filed: Feb. 27, 1995

Related U.S. Application Data

[63] Continuation of Ser. No. 241,992, May 12, 1994, abandoned.

[51] Int. Cl.[6] ............................. G01N 21/27; G01N 21/64
[52] U.S. Cl. ......................... 356/73; 356/417; 356/418; 250/458.1; 250/461.1; 348/81
[58] Field of Search .............................. 356/73, 317, 318, 356/417, 418; 250/458.1, 459.1, 461.1; 348/81

[56] References Cited

U.S. PATENT DOCUMENTS

| | | |
|---|---|---|
| 3,447,124 | 5/1969 | Louviere et al. . |
| 3,666,945 | 5/1972 | Frungel et al. . |
| 4,057,721 | 11/1977 | deVial et al. ............................. 250/301 |
| 4,170,987 | 10/1979 | Anselmo et al. . |
| 4,178,512 | 12/1979 | Frungel et al. ......................... 250/461.1 |

(List continued on next page.)

OTHER PUBLICATIONS

Alfred D. Thurston, Jr. and R. W. Knight, "Characterization of Crude and Residual–Type Oils by Fluorescence Spectroscopy", *Environmental Science & Technology*, vol. 5, No. 1, Jan. 1971, pp. 64–69.

Joseph D. Germano and Donald C. Rhoads, "REMOTS® Sediment Profiling at the Field Verification Program (FVP) Disposal Site", pp. 536–544, in ASCE Proceeding of the Conference *Dredging '84* (14–16 Nov. 1984).

(List continued on next page.)

*Primary Examiner*—F. L. Evans
*Attorney, Agent, or Firm*—Banner & Witcoff, Ltd.

[57] ABSTRACT

A spectrometer system includes a processing center, an underwater remote sensor and a communication link coupled therebetween. The sensor is deployed to at least partially penetrate a sediment layer disposed beneath a body of water. The sensor includes a window defining a sediment window plane through which a profile of the sediment layer is observable and a camera, an image plane of which is a conjugate of the window, the camera imaging light from objects in the sediment window plane to generate imagewise data, the imagewise data being transmitted over the communications link to the processing center. The sensor also includes at least one removable cell disposed in the sediment window plane, each removable cell being comprised of a transparent solid material having a void therein, the void in each removable cell for holding a standard material corresponding to the respective removable cell. The sensor further includes a camera filter device having at least one camera filter. Each camera filter is characterized as passing radiant energy within a corresponding emission band of camera wavelengths, the camera filter device being controllable to select a current camera filter. The sensor further includes an illumination source to produce radiant energy and an illumination filter device having at least one illumination filter. Each illumination filter is characterized as passing radiant energy within a corresponding illumination band of wavelengths. The sensor further includes a blocking filter device having at least one blocking filter, each blocking filter being synchronously coordinated with a corresponding illumination filter to block light in the illumination band from reaching the camera.

68 Claims, 13 Drawing Sheets

U.S. PATENT DOCUMENTS

| | | | |
|---|---|---|---|
| 4,293,225 | 10/1981 | Wheaton et al. | 356/417 |
| 4,434,364 | 2/1984 | Correa et al. | 250/253 |
| 4,446,370 | 5/1984 | Gergely | 250/301 |
| 4,515,165 | 5/1985 | Carroll. | |
| 4,556,057 | 12/1985 | Hiruma et al.. | |
| 4,887,040 | 12/1989 | Murray et al. | 324/446 |
| 4,942,303 | 7/1990 | Kolber et al. | 250/458.1 |
| 5,049,738 | 9/1991 | Gergely et al. | 250/301 |
| 5,075,172 | 12/1991 | Dixon et al. | 428/422 |
| 5,128,882 | 7/1992 | Cooper et al. | 364/550 |
| 5,270,644 | 12/1993 | Rhoads et al.. | |
| 5,422,730 | 6/1995 | Barlow et al. | 356/417 |

OTHER PUBLICATIONS

V. Zitko and W. V.Carson, "The Characterization of Petroleum Oils and Their Determination in the Aquatic Environment", *Fisheries Research Board of Canada*, Technical Report No. 217, 1970, pp. 1–29.

Donald C. Rhoads and Joseph D. Germano, "The Use of Remots Imaging Technology for Disposal Site Selection and Monitoring", *Geotechnical Engineering of Ocean Waste Disposal*, American Society for Testing and Materials, 1990, pp. 50–64.

Dr. Joseph D. Germano, "High Resolution Sediment Profiling With REMOTS Camera System", *Sea Technology*, Dec. 1983, pp. 33–41.

B. D. S. O'Connor, J. Costellose, B. F. Keegan and D. C. Rhoads, "The Use of Remotes Technology in Monitoring Coastal Enrichment Resulting from Mariculture", *Marine Pollution Bulletin*, 1989, pp. 384–390.

Donald C. Rhoads and Joseph D. Germano, "Interpreting Long-Term Changes in Benthic Community Structure: A New Protocol", *Hydrobiologia*, 142, Dr. W. Junk Publihers, Dordrecht, Netherland, 1986, pp. 291–308.

SAIC REMOTS Technology, brochure by SAIC, 1989.

Raymond M. Valente, Donald C. Rhoads, Joseph D. Germano and Victor J. Cabelli, "Mapping of Benthic Enrichment Patterns in Narragansett Bay, Rhode Island", *Estuaries*, vol. 15, No. 1, Mar. 1992, pp. 1–17.

Eugene C. Revelas, Joseph D. Germano, Donald C. Rhoads, "REMOTES®: Reconnaissance of Benthic Environments", *Coastal Zone '87*, ASCE, Mary 1987, pp. 2069–2083.

Donald C. Rhoads and Joseph D. Germano, "Characterization of Organism-Sediment Relations Using Sediment Profile Imaging: An Efficient Method of Remote Ecological Monitoring of the Seafloor (Remotes™ System)", *Marine Ecology-Progress Series*, May 7, 1982, vol. 8; 115–128.

Donald C. Rhoads, Joseph D. Germano and Larry F. Boyer, "Sediment Profile Imaging: An Efficient Method of Remote Ecological Monitoring of the Seafloor (*Remots*™ System)", *Ocean, Sep.* 1981, pp. 561–566.

"Sediment Profiling Camera System, Model 3731", Jan. 1985, p. 15 Benthos Catalog.

"Remote Sediment Profile Analysis", *Sea Technology*, Dec. 1983, p. 38.

"Optimization of the optical characteristics of a fiber-optic guided laser fluorescence technique for the in situ evaluation of fuels in soils", Sabine E. Apitz, et al., SPIE-Proceedings vol. 1637, *Environmental Process and Treatment Technologies*, 1992.

Dixon, B., et al., Chapter 10, "Electrochemiluinescent Optrode Development for the Rapid and Continous Monitoring of Petroleum Contamination", (pp. 111–124), *Petroleum Contaminated Soils*, vol. 3, Paul T. Kostecki and Edward H. Calabrese (editors), Lewis Publishers, Chelsea, Michigan, 1989.

Eastwood, D., et al., "An Overview of Advanced Spectroscopic Field Screening and In-Situ Monitoring Instrumentation and Methods", *Chemistry for the Protection of the Enviornment*, pp. 97–111, 1991.

Eastwood, D., et al., "Molecular Optical Spectroscopic Techniques for Hazardous Waste Site Screening", Project Summary EPS/600/S4–91/011, Sep. 1991.

EPA "Continuous Monitoring with Purge-and-Trap Gas Chromatography", Environmental Monitoring Systems Laboratory, Jul. 1991.

"In Situ Fluorescence Imaging of Sediment-Associated Hydrocarbons in Bioturbated Sediments", Marine Surveys, Inc., Report No. NSF/OCE-85004, Jul. 1985.

Inman, Scott M, et al., "Development of a pulsed-laser, fiber-optic-based fluorimeter: determination of fluorescence decay times of polycyclic aromatic hydrocarbons in sea water", *Analytica Chimica Acta*, 239 (1990), pp. 45–51.

Klainer, Stanley M. et al., "Environmental Monitoring Applications of Fiber Optic Chemical Sensors (FOCS)", *Fiber Optic Chemical Sensors and Biosensors*, Chapter 12, pp. 83–122, CRC Publishers.

Leonard, L. and Tilman, N., "Sensor Integration for Site Screening: Smart Weapons fo the Fight Against High Cost", paper given at Third International Symposium, *Filed Screening Methods for Hazardous Wastes and Toxic Chemicals*, Feb. 24–26, 1993.

Rhoads, D.C. and Cande, S., "Sediment Profile Camera for In Situ Study of Organism—Sediment Relations" *Limnology and Oceanography*, vol. 16, No. 1, Jan. 1971, pp. 110–114.

Milanovich, Daley, Klainer and Eccles, "Remote Detection of Organochlorides With a Fiber Optic Based Sensor: II A Dedicated Portable Fluorimeter", *Analytical Instrumentation*, 15(4), pp. 347–358 (1986).

"Down" Position Transecting the Sediment-Water Interface

On the Seafloor

Deployed

WHITE LIGHT 420 nm

430nm 450 nm 470 nm 490 nm 500 nm

METHODS AND APPARATUS FOR TAKING SPECTROSCOPIC MEASUREMENTS OF SEDIMENT LAYERS BENEATH A BODY OF WATER

This application is a continuation of application Ser. No. 08/241,992, filed May 12, 1994, now abandoned.

BACKGROUND OF THE INVENTION

1. Field of the Invention

The invention generally relates to methods and an apparatus for taking underwater spectroscopic measurements. In particular, the invention relates to the measurement and identification of contaminants in sediment layers by analysis of luminescent signatures of contaminants.

2. Brief Description of Related Art

Some existing sensor systems can acquire in-situ luminescence (fluorescence and phosphorescence) or UV/visible data in the field from soils or sediments. Of particular interest are sensors focused on penetration of solid-liquid media followed by in-situ imaging and measurement.

Fiber optic in-situ sensors have been developed for measuring fuels and other organic chemicals in terrestrial soils. No sensors have been developed for deployment in aquatic media for the purpose of sensing within the seabed, lake bed, or the bottom of rivers. The in-situ soil sensors generically consist of (1) an above ground power source, incandescent or laser excitation light source, a light control unit, data logger, display and processing sensor unit; and (2) a fiber optic cable which serves to both transmit the excitation light into the soil and collect and transmit the signal up to the sensor unit, the fiber optic cable being inserted into the soil by means of a cone penetrometer or is lowered into a pre-drilled test hole.

A recent review of fiber optic chemical sensors is presented in Klainer et al., *Environmental Monitoring Applications of Fiber Optic Chemical Sensors (FOCS)*, Vol. II, Chapter 12, CRC Publishers, (1991). Two portable prototype spectrometers are described. One of these consists of an incandescent lamp illumination source and a photodiode detector. The emitted light entering the optical splitter is filtered so only one wave length band is emitted. This excitation wave length band is then split by a dichroic mirror separating the excitation from the UV emission bands. The signal channel is detected by a photodiode. The area of measurement is dictated by the diameter of the optical fibers and can be from 100 to 600 µm in diameter (Milankovich, Daley, Klainer and Eccles, "Remote Detection of Organochlorides With Fiber Optic Based Sensor, II. A Dedicated Portable Fluorimeter", *Anal. Instrum.*, 15, 347 pp., 1986).

The second portable spectrometer described by Klainer et at., (1991) is designed to measure fluorescence or change in refractive index (Douglas Instruments Co., Palo Alto, Calif.). This spectrometer uses a miniature optical bench, a small adjustable output tungsten halogen lamp, an adjustable light path for critical alignment, optical band-pass filters to provide a narrow excitation beam, a dichroic beam splitter, and a photodiode to respond to 300 to 1600 nm excitation wave lengths. The excitation signal is passed through a preamplifier to a signal data acquisition system.

Another view of portable spectrometers is given in Eastwood, Lidberg, Simon and Vo-Dinh "An Overview of Advanced Spectroscopic Field Screening and In-Situ Monitoring Instrumentation and Methods," *Chemistry for the Protection of the Environment*, Plenum Press, New York, (1991) and Eastwood and Vo-Dinh, *Molecular Optical Spectroscopic Techniques for Hazardous Waste Site Screening*, EPA/600/S4-91/011, September, 1991. The authors indicate that, at the date of publication, only two truly portable fluorimeters existed. One is the Baird Field Identification Luminoscope Monitor (FILM), manufactured for the Coast Guard to detect oil and hazardous chemicals in water. It operates off a 12 v dc battery and uses a mercury lamp with a 254 nm line isolated for excitation. The emission spectrum (250 to 600 nm) is dispersed by a flat field grating and recorded on polaroid film. The second portable system is called the L-101A Fiber Optic Luminoscope (Environmental Systems Corporation). This system also uses a mercury lamp for excitation but isolates the 365 nm or other Hg line. The excitation light is focused onto a bifurcated fiber-optic lightpipe and is transmitted to a probe which can be placed against soil surfaces or into water. The returning emission is then directed into a manually scanned monochrometer with photomultiplier detection.

Another fiber optic system, not described in the above reviews, is the pulsed nitrogen laser fiber-optic fluorimeter (Inman, Thibado, Theriault and Lieberman, "Development of a pulsed-laser, fiber-optic-based fluorimeter: determination of fluorescence decay times of polycyclic aromatic hydrocarbons in seawater", *Analytica Chimica Acta*, Elsevier Science Publishers B. V., Amsterdam, 239 (1990) pp. 45–51. This system uses excitation light provided by a pulsed nitrogen laser with a pulse width of 3 ns and a pulse energy of 300 µJ. The pulsed light is passed through a beam splitter and about 80% of this light enters a 10 m length of 325 µm diameter UV-grade fiber. Some of the excitation light is passed through a beam splitter and directed toward an avalanche photodiode to determine the time of firing of the laser in order to gate the detector. Six receiver fibers are concentrically arrayed around the central excitation fiber. The emission signal is then transmitted through collimating optics and the signal is fed into a compact spectrograph with a 300 groove/mm holographic grating. A filter blocks the emission spectrum below about 400 nm. The emission spectra are measured with a diode array. The output yields a spectral range of ca. 350 nm with a resolution of 0.5 nm/pixel. The time-resolved analysis requires binning of pixels by 10, decreasing the spectral resolution to 5 nm but reducing noise and increasing sensitivity. This system has been coupled to a cone penetrometer and is pushed into compact soils by a hydraulic piston (Apitz, Theriault, and Lieberman, "Optimization of the optical characteristics of fiber-optic guided laser fluorescence technique for the in-situ evaluation of fuels in soils", SPIE, The International Society for Optical Engineering, Proceeding Vol., 1637, present at OE/LASE, 22 Jan. 1992, Los Angeles, Calif.). This general concept of integrating a spectrometer into a soil penetrating probe is covered in U.S. Pat. No. 5,128,882 granted to Cooper and Malone in 1992. In both the Apitz and Theirault, and Lieberman, 1992 system and that described in the Cooper and Malone, the spectrometers measure luminescence through an optical fiber over a small diameter window. Neither of these systems contain reference standards within the window probe.

A chemical electroluminscence electrode (U.S. Pat. No. 5,075,172 to Dixon et al., granted 1991) has been developed for rapid screening of contaminated ground water for aromatic hydrocarbons (esp. benzene). This system consists of an electrochemical optical fiber; an optrode sensor coated with ruthenium bipyridyl which registers an increase in light emission (500 to 700 nm) when in contact with aromatic hydrocarbons in ppb (parts per billion) concentrations (Dixon et al., "Electrochemiluminescent Optrode Development for the Rapid and Continuous Monitoring of Petroleum Contamination", *Petroleum Contaminated Soils*, Vol. 3, (Kostecki, et al., editors) chapter 10, pp. 111–124, Lewis Publishers, Chelsea, Michigan 48118, 1990). A proposed (not existing) prototype field instrument would consist of a small PVC pipe containing the optrode sensor and light detector electronics that could be lowered into a test well. All recording equipment is located above ground.

Non-fiber optic based field sensors have been developed to measure volatile organic compounds (VOC) in soils at Superfund Sites. These include Purge-and-Trap Gas Chromatography. The Purge-and-Trap or continuous flow gas system may also be coupled with fiber optic sensors (Leonard and Tillman, "SENSOR INTEGRATION FOR SITE SCREENING: Smart Weapons for the Fight Against High Costs", present at Third International Symposium: Field Screening Methods for Hazardous Wastes and Toxic Chemicals, held February 24–26, 1993, Sands Hotel, Las Vegas, Nev.). This involves the insertion of a gas permeable sampling vessel into the ground via a penetrating tool. Several of these can be deployed over the area of interest. A soil-gas sampling line connects the gas permeable sampling vessel to the surface where a sampling manifold allows for on-line intake of gas samples from different collection points. An injector inserts the sample into a portable gas chromatographic analyzer and analysis is done in real time. (*Volatile Organic Compounds in Water by Purge and Trap Capillary Column Gas Chromatography with Photoionization and Electrolytic Conductivity Detectors in Series*, Method 502.2, U.S. EPA, Cincinnati, 1986).

Many aquatic environments contain particulate organic matter which eventually settles forming a deposit on the bottom. Some of these particles can be associated with organic contaminants including hydrocarbons. Assessment of organic pollution of the seafloor, lake, or river bottom is required in many environmental monitoring studies. Once particle associated contaminants settle to the bottom, they may be buried by new sediment or biologically mixed Coioturbated) into the bottom to depths of a few 10's of centimeters. Sediment quality assessment therefore requires imaging and measurement of contaminates within the biologically active zone of the bottom (usually ≦25 cm). Sources of contamination may be inferred from the spatial relationship of fluorescent contaminants to imaged dredge material layers, sewage sludge layers, oil globules, or deposits proximal to industrial/municipal effluent, or atmospheric sedimentation from combustion sources.

This disclosure addresses the need for developing a rapid chemical screening tool by describing an instrument that can collect, in near real-time, in situ chemical information from an upper sediment column. This field reconnaissance measurement technique may be used to map temporal/spatial gradients of organic contaminants in aquatic sediments.

This invention is based on the concept of sediment-profile imaging as first described and practiced by Rhoads and Cande "Sediment Profile Camera For In Situ Study of Organism-Sediment Relations," *Limnology and Oceanography*, Vol 16, No. 1, pp. 110–114, (1971). This invention improves and extends the concept to include UV spectrometry (fluoroscopy). A detailed description of the Rhoads-Cande camera was publicly disclosed in the 1971 journal reference and a patent was never applied for. The Rhoads-Cande profile camera was based on a still film camera using off-the-shelf black and white negative or color transparency film and visible light for illumination. The Rhoads-Cande photographic profile camera is used to image biological and physical structures in the upper 20 cm of the bottom but the system does not have the capability to make chemical measurements.

SUMMARY OF THE INVENTION

It is an object of the present invention to provide an imaging chemical sensor for sensing chemicals in a sediment layer beneath a body of water. It is yet another object of the invention to provide a remote sensor which produces measurement signals for transmission to a processing center, the measurement signals being transmitted in a manner which does not attenuate signal strength.

It is yet another object of the invention to provide rapid in situ measurements on fluorescing materials in the sediment layer. It is yet another object to provide excitation energy at a plurality of illumination bands for inducing fluorescence of visible wavelengths. It is yet another object to provide a system for estimating a concentration of the fluorescent compounds. It is yet another object to provide a system for qualitatively identifying the fluorescing species. It is yet another object to provide a system for developing a fluorescing spectrum of the fluorescing compounds. It is yet another object to provide a sensor for collecting emission spectra of the fluorescing compounds within specific preselected and discrete spectral bands of wavelengths.

It is yet another object of the invention to provide an imaging sensor for measurement of contaminants within the sediment layers where the area of the image is sufficiently large to relate the distribution of the contaminants to structural features in the sediment layer including such features as dredged material layers, an oil spill layer and a depth of the biologically mixed layer. It is yet another object of the invention to provide an estimate of the depth of the reduction/oxidation potential discontinuity layer. It is yet another object of the invention to relate contaminant signatures with stratigraphy to aid in interpreting how the contaminants are introduced into the environment. It is yet another object to provide a sensor where standard reference samples are disposed within the field-of-view of the sensor.

It is yet another object of the invention to provide a system where a survey crew can obtain immediate feedback of information to allow cost-effective and parsimonious sampling of the sediment layers. It is yet another object of the present invention to provide a system to aid the survey crew in avoiding over-sampling and under-sampling of a survey area.

These and other objects are achieved in a spectrometer system which includes a processing center, an underwater remote sensor and a communication link coupled therebetween. The sensor is deployed to at least partially penetrate a sediment layer disposed beneath a body of water. The sensor includes a window defining a sediment window plane through which a profile of the sediment layer is observable and a camera, an image plane of which is a conjugate of the window, the camera sensing light from the sediment window plane to generate imagewise data, the imagewise data being transmitted over the communications link to the processing center. The sensor also includes at least one removable cell disposed in the sediment window plane, each removable cell being comprised of a transparent solid material having a void therein, the void in each removable cell for holding a standard material corresponding to the respective removable cell. The sensor further includes a camera filter device having at least one camera filter. Each camera filter is characterized as passing radiant energy within a corresponding emission band of camera wavelengths, the camera filter device being controllable to select a current camera filter. The sensor further includes an illumination source to produce radiant energy and an illumination filter device having at least one illumination filter. Each illumination filter is characterized as passing radiant energy within a corresponding illumination band of wavelengths.

The processing center controls the sensor to collect a plurality of data sets, each data set corresponding to the imagewise data. The processing center processes the plurality of data sets to produce a normalized data set, an estimate of the concentration of a contaminant found within the sediment layers, a spectrum of the contaminant found within the sediment layers, and an identification of the contaminant species.

BRIEF DESCRIPTION OF THE DRAWINGS

The invention will be described in detail in the following description of preferred embodiment with reference to the following figures wherein.

DETAILED DESCRIPTION OF PREFERRED EMBODIMENTS

The remote sensor of the invention is a device lowered into an aqueous medium penetrating the sea bed, lake bottom or stream bed. The sensor images the sediment-water interface and the underlying sediment column over a large area (e.g., fifteen by twenty centimeters) in vertical profile as a set of three images (red, green and blue) utilizing approximately white light. The system then illuminates the same prof fie with radiant energy in the ultraviolet (UV) range and collects UV and visible luminescence/phosphorescence with an imaging sensor, preferably a CCD camera, over a wide range of wavelengths (e.g., 360–600 nm) utilizing appropriate blocking filters to exclude excitation bands (i.e., wavelengths used to excite fluorescence). The imaged sediment profile contains, at the top of the field of view, a series of pre-prepared standards in small water-tight cells. These standards may include contaminant free sediment (i.e., a blank sample) while other cells may be spiked to contain known concentrations of known hydrocarbons or other suspected contaminants. These blanks and references can be removed and replaced with other blanks and references depending on the target compound(s) of interest. The blank spectrum is used to correct the raw spectra as measured in the sediment to produce a normalized spectra. The spiked references are used to generate a graph relating intensity of fluorescence to gravimetric concentration of a known contaminant and for identification or classification of compounds. The blank and standards also serve to assess the precision and accuracy of the spectrometer. The spectral signatures of the imaged profile are passed to the surface along with the conventional RGB color image through an electrical conducting or optical fiber cable and displayed on a spectral and image analysis unit (e.g., the display of controller 42 shown in FIG. 3) in a processing center aboard a survey vessel. Imaged structures such as dredged material layers, sewage sludge deposits, oil globules, and other types of sedimentary fabrics can then be related to imaged patterns of fluorescence at particular excitation and emission wavelengths.

Figure 2C:
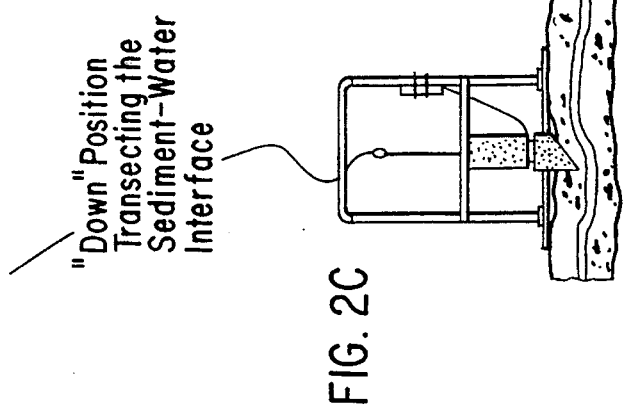
FIGS. 2A–2C are schematic diagrams showing a representative sensor deployment according to the present invention.
Figure 2B:
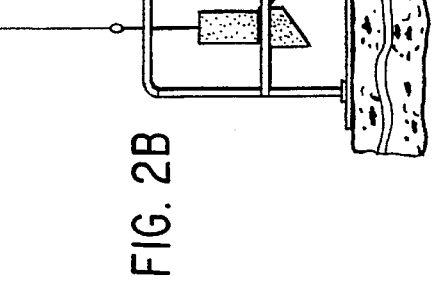
Figure 2A:
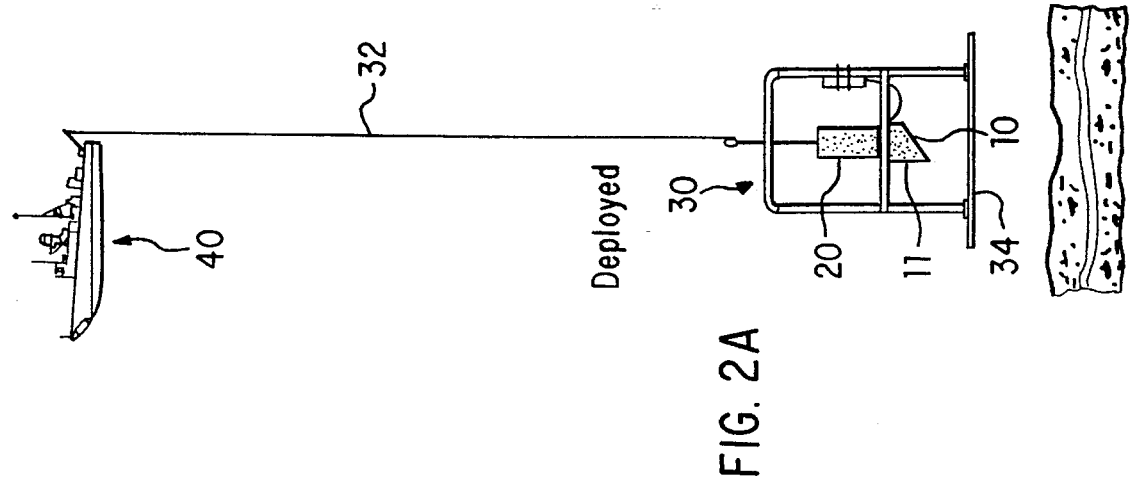

FIGS. 2A–2C show the sensor deployment and measurement sequence. Sensor assembly 30 is lowered through the water column with a support/power/signal cable 32. While tension is exerted on the cable, as depicted at in FIG. 2A, the optical prism of sensor 20 is held in an "up" position above base frame 34. This is necessary to avoid disturbance of the bottom by a pressure wave below the prism as the base frame settles onto the bottom as depicted in FIG. 2B. As the cable becomes slack, the optical prism/sensor assembly is passively lowered into the bottom at a slow rate (about 5 centimeters per second) to avoid resuspending the surface of the bottom to be profiled and imaged as depicted in FIG. 2C. The slow rate-of-descent is accomplished by transferring oil through a small hole in a piston assembly. Once the optical prism (i.e., inverted periscope) has fully penetrated into the bottom and stopped its descent, the shipboard controller on the vessel initiates measurement of the sediment profile through communication cable 32.

Figure 3:
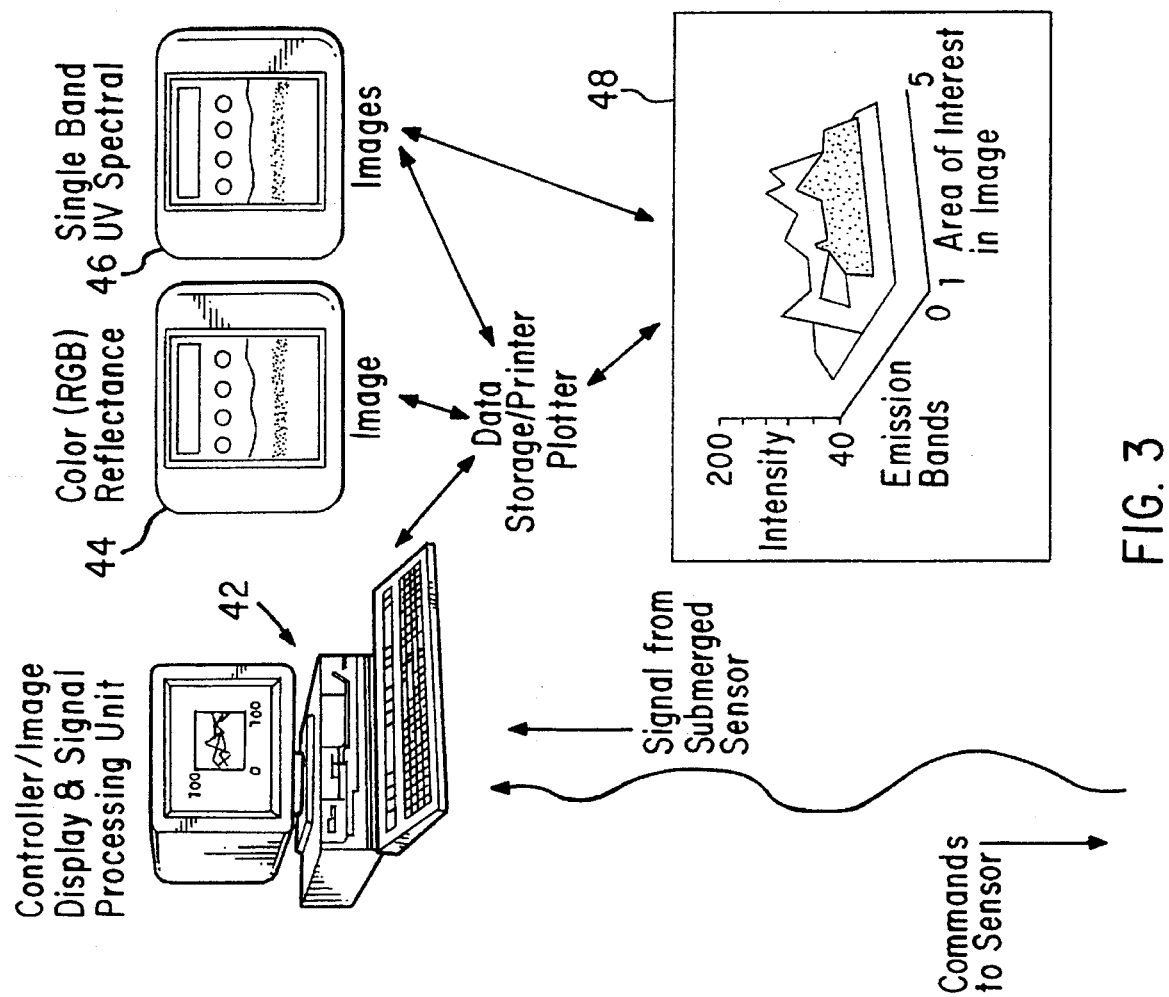
FIG. 3 is a schematic diagram of a processing center onboard a survey vessel.

FIG. 3 shows the system elements contained onboard survey vessel 40. The measurement sequence is initiated from the controller 42. First, the CCD camera produces a conventional color reflectance image of the sediment profile by successively using a set of red, green and blue (RGB) transmission filters matched to the human eye's response. Three data sets corresponding to the red, green and blue filtered imagewise data is transmitted from sensor 30 to controller 42. Controller 42 combines the three data sets to form the color image. This image is viewed as depicted at 44, recorded, and stored in a memory unit, preferably a magnetic disk storage device. Controller 42 then commands the sensor to initiate the fluorescence spectroscopy by first selecting a specific illumination (or excitation) band. Thereafter, a series of emission (referred to as camera) wavelengths are sequentially selected. While each camera wavelength is selected, the imagewise data from the camera is collected and displayed as depicted at 46, and stored for each emission (i.e., camera filter) wavelength. Thereafter, additional excitation bands may be selected and the measurement process repeated. Spectral processing is accomplished through controller 42 by recalling the emission wavelengths from memory for a given excitation band. A three dimensional summary of the data is assembled for comparing the intensity of each emission spectrum for imaged areas (i.e., sedimentary features and reference cells) identified by a user of interest as depicted at 48. The imaged fluorescence 46 can be spatially related to the RGB image of sedimentary structures (strata, organism burrows, sludge layers, oil globules, etc.) by overlaying the RGB (i.e., color) image depicted at 44 with individual emission spectra depicted at 46, or the summed emission spectra (e.g., each pixel being summed over all emission wavelengths to produce a corresponding total pixel). Hard copies of the images, spectra, or tabular data may be printed out on a printer or plotter.

Figure 5:
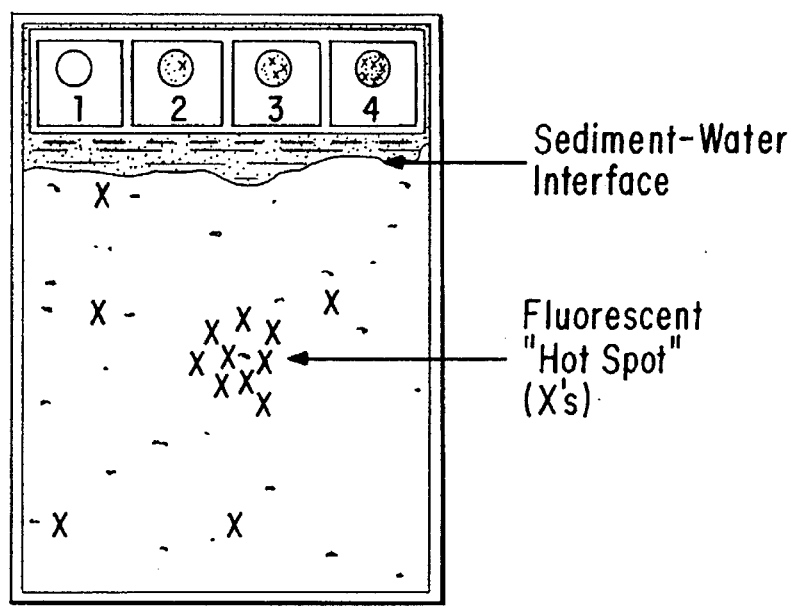
FIG. 5 is a representative sediment profile as recorded by the sensor camera.

FIG. 5 shows the imaged sediment profile as recorded by the CCD camera. At the top of the imaged window are several reference samples that have been prepared in advance of the sensor survey. One of these cells (e.g., #1) contains a sample of the sediment of interest which represents a "blank" (i.e., natural sediment typical of the survey area but with a low background of contamination). The spectra obtained from this blank are subtracted from all other measurements. The blank is prepared by mixing a small aliquot (i.e., a portion) of sediment with pure seawater and the mixture is placed into a removable cell such as a depression slide. A quartz cover slip is cemented over the blank sample. This slide is placed into a holder that frankly holds the reference blank against the front of the quartz optical window. Reference cells 2, 3, 4, . . . n represent natural sediments from the survey site which have been "spiked" with known concentrations of hydrocarbon contaminants of interest. These may be the same compound in different concentrations or different compounds at the same concentration. The reference standards and blank sample at the top of the imaging window shown in FIG. 5 allow assessment of accuracy precision, and performance of the sensor system in real time and also provide spectral signatures for normalizing measurements by blank subtraction. The reference standards are also used to develop a contaminant concentration versus emission intensity graph.

A spectrum of the fluorescence response to the excitation illumination for each of the reference standards and any selected area within the sediment profile may be obtained. Each spectral image is first normalized with the blank sample. A spectrum for a particular reference standard is then obtained by recording the intensity of the portion of the spectral image at the position within the image of the particular reference standard for each spectral image (i.e., for data sets of each camera filter). The spectra obtained for the normalized reference standards are used to identify unknown contaminants imaged and measured in the sediment column such as areas marked by Xs in FIG. 5. Areas of intense fluorescence in the sediment column ("hot spots" as shown by Xs in FIG. 5 relative to non-fluorescing ambient sediment) are designated by a user as the focus for spectral analysis by the display and signal processing unit (i.e., controller 42). The depth of such hot spots in the sediment column can be measured from the sediment-water interface datum shown in FIG. 5 as observed in the RGB or fluorescence images. The RGB image also allows one to relate hot spots to imaged structures such as dredged material layers or sludge.

Figure 1:
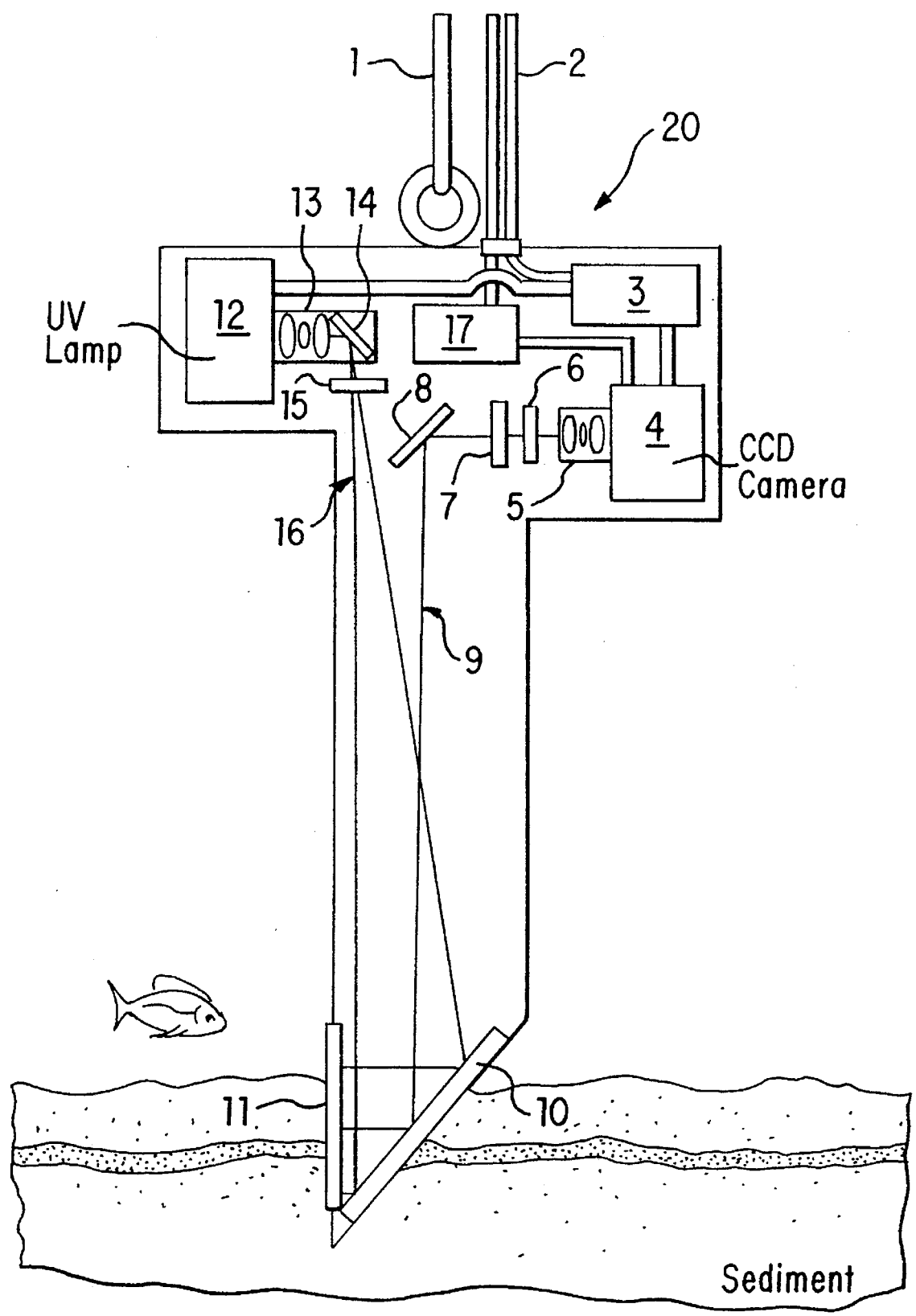
FIG. 1 is a schematic diagram of a sensor according to the present invention.

FIG. 1 is a schematic drawing of the key sensor components. Sensor 20 is lowered to the bottom by support cable 1 (one of two cables of communications cable 32 in FIG. 2A). Cable 32 also links the shipboard power source and communication to sensor 20 by cable 2 (another of the two cables of communications cable 32 in FIG. 2A). Cable 2 carries electric power and electrical and optical signals. The power is conditioned in electrical unit 3 and distributed to camera 4 and lamp 12. Electrical unit 3 also executes commands from shipboard controller 42 to sensor 20 to control camera and lamp functions. The CCD camera is fitted with photographic lens 5 with an appropriate focal length for optical path 9. Camera filter device 6 is preferably located in front of lens 5. Camera filter device 6 includes a set of emission bandpass filters (i.e., camera filters). Long pass filter 7 (also referred to as blocking filter 7) is located in front of camera filter device 6 to exclude or block excitation wavelengths (i.e., UV light) emitted from lamp 12.

The camera emission filters are preferably contained within a mechanized filter wheel and rotated sequentially to obtain discrete spectral images. The first three filters in the wheel are, for example, the red, green, and blue (RGB) filters for conventional color reflectance imaging. The balance of the filters, for example 17 in number, are for collecting fluorescence images at preselected wavelengths and bandpass intervals, preferably 10 nm wide bandpass intervals per filter.

First surface mirrors 8 and 10 are used to bend the optical path from quartz window 11 to the CCD camera so that the camera, optical path and mirrors enable an image of window 11 to be present in the focal plane. Light emitted from this image will be sensed by the camera to produce imagewise data for transmission over cable 2. When sensor 20 is deployed in a sediment layer beneath a body of water, window 11 allows camera 4 to image a profile of the sediment layer. A lamp 12, preferably a mercury lamp rich in UV emissions, is used for illumination through collimating optics 13 and a dichroic folding mirror 14. Illumination filter device 15 is preferably a mechanized filter wheel containing UV excitation band pass filters which are used to define a plurality of narrow excitation bands. This step is preferably coordinated with an appropriate blocking filter 7. The selected excitation illumination is directed through ray path 16 onto the sediment profile after reflection at mirror 10 and passage through quartz window 11. It will be appreciated that the camera optics may have an appreciable depth of field about the plane of window 11 so that objects at or near the plane of window 11 remain in focus. The RGB and fluorescence images are collected by the CCD camera, temporarily stored in buffer 17, and transmitted to the surface for display and image processing by controller 42 of the processing center aboard the survey vessel.

The imagewise data is preferrably digital data comprising an image header and one or more packed binary data blocks. In a prototype sensor, camera 4 contained a two dimensional CCD focal plane array organized as an array of 512 by 512 individual pixel sensors. Each pixel sensor generated a 16 bit binary word, in two 8 bit bytes, representative of the light intensity impinging on the pixel during a particular sensing time, although not all bits of the 16 bit word contained significant data. Thus, the two dimensional CCD focal plane array generated imagewise data having 524,288 bytes per image plus header data.

Camera 4 is preferably a multimode camera having a capability to operate in a lower spatial resolution configuration. For example, the focal plane array may be organizable into a array of 256 by 256 virtual pixel sensors, where each virtual pixel sensor is comprised of a 2 by 2 array of actual pixel sensors. This has the advantage of improving detection sensitivity for a specified signal to noise ratio at the cost of reducing spatial resolution of the image depicted in the imagewise data. With such a virtual mode, camera 4 would generate imagewise data having 131,072 bytes per image, each virtual pixel sensor would have four times the detection sensitivity, as it would subtend four times the spatial area of an actual pixel sensor. The ability to programmably increase the detection sensitivity of the camera, even at the cost of spatial resolution, permits the sensor to be used for surveying sediment layers for low concentrations of suspected contaminants and still limit the time that the sensor is deployed in the sediment.

Figure 4:
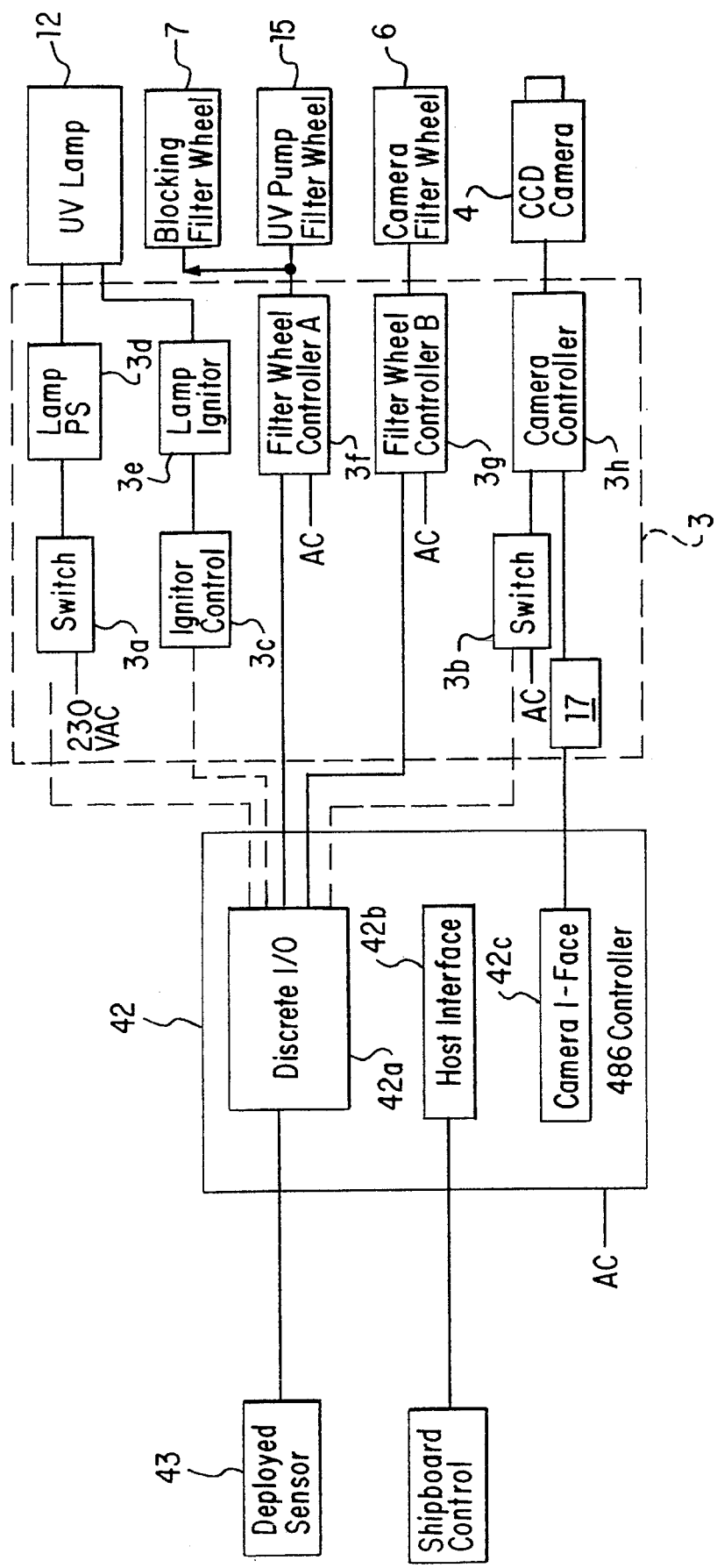
FIG. 4 is a functional block diagram of the spectrometer system.

FIG. 4 is a functional block diagram of the spectrometer system. In FIG. 4, controller 42 of the processing center includes Discrete I/O 42a, Host Interface 42b and Camera Interface 42c. Discrete I/O 42a outputs an output signal connected to deployed sensor indicator 43, preferably an indicator lamp. Discrete I/O 42a also outputs a plurality of discrete output signals to electrical unit 3. At least one of the plurality of discrete output signals is a signal for turning on and off power to lamp 12. At least one other of the plurality of discrete output signals is a signal to control the lamp ignitor for lamp 12. At least one other of the plurality of discrete output signals is a signal to turn on and off power to camera 4. At least one other of the plurality of discrete output signals is a signal to control the operation of camera 4. At least one other of the plurality of output signals is a signal to control illumination filter device 15. At least one other of the plurality of output signals is a signal to control camera filter device 6. At least one other of the plurality of output signals is a signal to control blocking filter device 7. Blocking filter device 7 is preferably synchronously coordinated with illumination filter device 15.

Illumination, camera and blocking filter devices 15, 6 and 7 may output discrete indicator signals to Discrete I/O 42a through electrical unit 3. Furthermore, camera 4 may output at least one indicator signal to Discrete I/O 42a through electrical unit 3, and illumination source 12 may preferably output at least one indicator signal to Discrete I/O 42a through electrical unit 3. Camera 4 outputs imagewise data to buffer 17. Buffer 17 outputs the imagewise data to camera interface 42c. Electrical unit 3 includes switch 3a to regulate power to illumination source 12, switch 3b to regulate power to camera 4, ignitor control 3c to control lamp ignitor 3e, lamp power supply 3d, A and B filter wheel controller 3f and 3g, and camera controller 3h. Filter wheel controller 3f preferably controls UV Pump (i.e., illumination) Filter Wheel 15 in synchronism with Blocking Filter Wheel 7.

A prototype spectrometer system has been developed for testing purposes. A high intensity UV-rich lamp is used to illuminate the sediment profile. A plurality of illumination filters contained in illumination filter device 15 exclude all visible light and pass radiant energy only in corresponding discrete UV excitation bands. For example, one filter in the prototype is characterized as passing radiant energy within an illumination (i.e., excitation) band defined to be at or near 314 nanometers (a UV wavelength). For the RGB imaging step, the illumination filter is preferably a long pass filter, blocking only UV wavelengths while passing visible wavelengths so the RGB images correspond to reflectance and not fluorescence.

The prototype sensor included an electrically cooled UV-sensitive CCD camera. The camera was used for conventional RGB color imaging and for collecting discrete emission spectra. In addition to the red, green and blue filters used for conventional RGB imaging, 17 additional 10 nm wide discrete (i.e., non-overlapping) spectral emission band filters were provided in camera filter device 6. Appropriate illumination (i.e., excitation) and blocking filters were contained in mechanized filter wheels of illumination filter device 15 and blocking filter device 7, respectively.

Although, the prototype contained three illumination filters and corresponding blocking filters, any number may be provided to meet specified sensor design requirements. Except for RGB imaging, the blocking filters prevent an image from being produced without fluorescent compounds being present in the field of view (sediment column), the fluorescent compounds converting excitation UV bands into visible light.

Figure 7A:
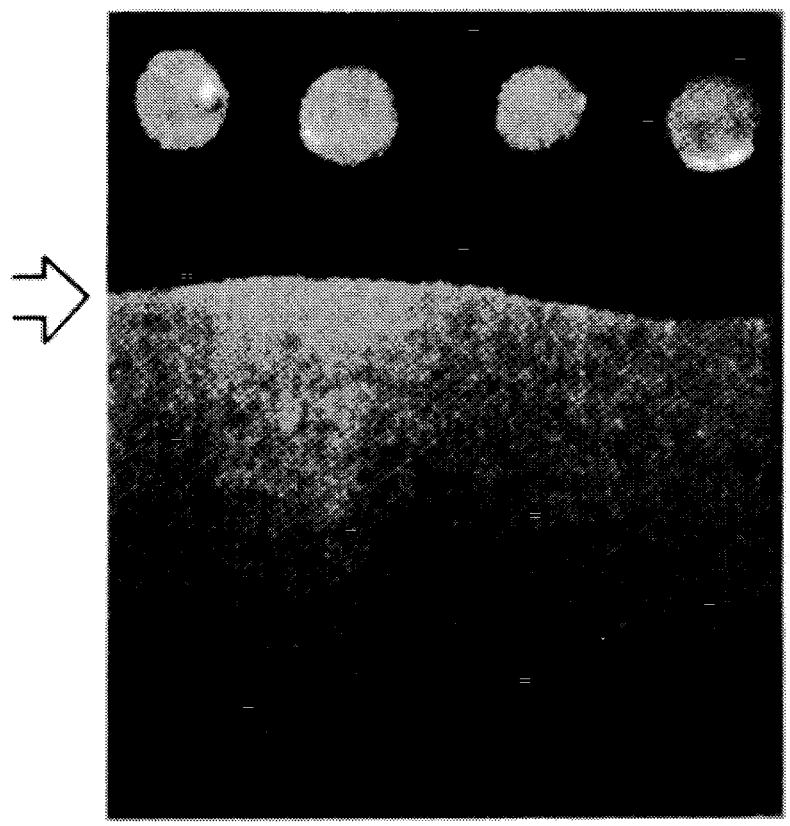
FIG. 7A is an example of a white light image produced by the spectrometer system.

In operation, remote sensor 20 was commanded by controller 42 to collect three data sets which constitute RBG image data. First, illumination filter device 15 was controlled to select a long pass filter as the current illumination filter so as to block UV radiant energy while passing visible light. This avoids fluoroscopic excitation of compounds in the sediment layer which may distort the RBG color image. Next, controller 42 controlled camera filter device 6 to select one of a red filter, a green filter, and a blue filter. Thereafter, with the sediment layer illuminated with visible light, camera 4 imaged the sediment layer to produce imagewise data corresponding to the filtered image, filtered according to the current camera filter. The imagewise data was temporarily stored in buffer 17 before it was transmitted over cable 2 to controller 42. The data collection process was then repeated for each of the other filters of the red, green and blue filters. When all three data sets had been transmitted to controller 42, controller 42 combined the data sets to produce the color image displayed at 44. A black and white example of this "white light" color image is shown in FIG. 7A. FIG. 7A shows a sediment-water interface line with an arrow. Four moon-like objects above the interface line correspond to the image of the blank sample and "spiked" reference standards contained in replaceable cells. In the prototype, the replace, able cells were depression-type microscope slides. The appropriate sediment samples were placed in the depression (i.e., void) and a quartz cover slip was cemented to hold in the sediment sample. The sediment samples, wet with the ambient sea water, were disposed in the void to match the sediment being imaged.

The reduction/oxidation potential of a point within the sediment is a voltage at that point within the sediment compared to a voltage of nearby seawater, and the reduction/oxidation potential typically varies between −200 millivolts and +200 millivolts depending on the quantity of oxygen in the sediment layer. The quantity of oxygen in the sediment layer is an indication of the presence of pollution in the sediment. Some chemical compounds, particularly iron chemical compounds, in the sea bed develop surface coatings which transfer from one oxide state to another depending on the reduction/oxidation potential. In many instances, the different oxide states express different colors (e.g., the different oxide states of iron express different colors). The RGB image developed by the spectrometer system measures this color in order to determine the apparent reduction/oxidation potential in the sediment.

Controller 42 then controlled illumination filter device 15 to select a different illumination filter. For example, in a prototype test, illumination filter device 15 was controlled to select an illumination filter which passed UV radiant energy having a wavelength of 314 nm while blocking filter device 7 was controlled to select a blocking filter to exclude 314 nm wavelengths passing through the illumination filter. The prototype sensor also included two additional illumination filters so that illumination filter device 15 could be controlled to pass any one of three UV excitation bands. In the prototype sensor, camera filter device 6 included a red filter, a green filter and a blue filter plus 17 discrete emission band filters. FIGS. 7B–7G show images produced using six of the filters, the six filters being characterized as passing emission (i.e., camera) bands having wavelengths of 420, 430, 450, 470, 490, and 500 nanometers. Controller 42 controlled camera filter device 6 to select a first camera filter as the current camera filter, for example, the filter passing radiant energy having wavelengths of 420±5 nm. Controller 42 then controlled camera 4 to image the sediment layer for fluorescing compounds. Camera 4 produced imagewise data which was temporarily stored in buffer 17 before being transmitted to controller 42. This imaging process was repeated for each of the other camera filters. FIG. 7B–7G illustrate examples of spectral images from a test sediment layer, the spectral images collectively being depicted as images displayable at 42 (FIG. 3).

In FIGS. 7B–7G the intensity of the image is displayed on a grey scale, the darker shades of grey corresponding to greater intensity. In these figures, normalized intensities varied from 80 to 600 (in arbitrary units) and were binned in five bins: 80–125, 125–350, 350–450, 450–500 and 500–600. Each bin was assigned a distinct shade of grey. It will be obvious to persons skilled in the art that a larger number of bins may be employed, and when the number of bins is very large, the image will approach a continuous tone image. With a limited number of bins and a color display device available, the bins are preferably assigned a unique color instead of a unique shade of grey.

Figure 7B:
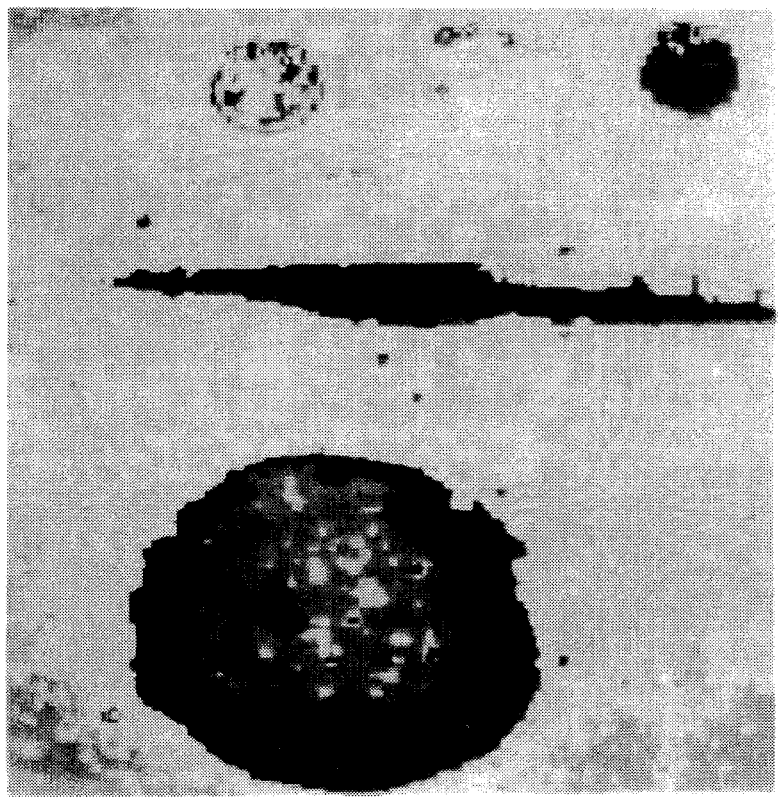
FIGS. 7B–7G are examples of spectral images of a fluorescing contaminant produced by the spectrometer system.
Figure 7C:
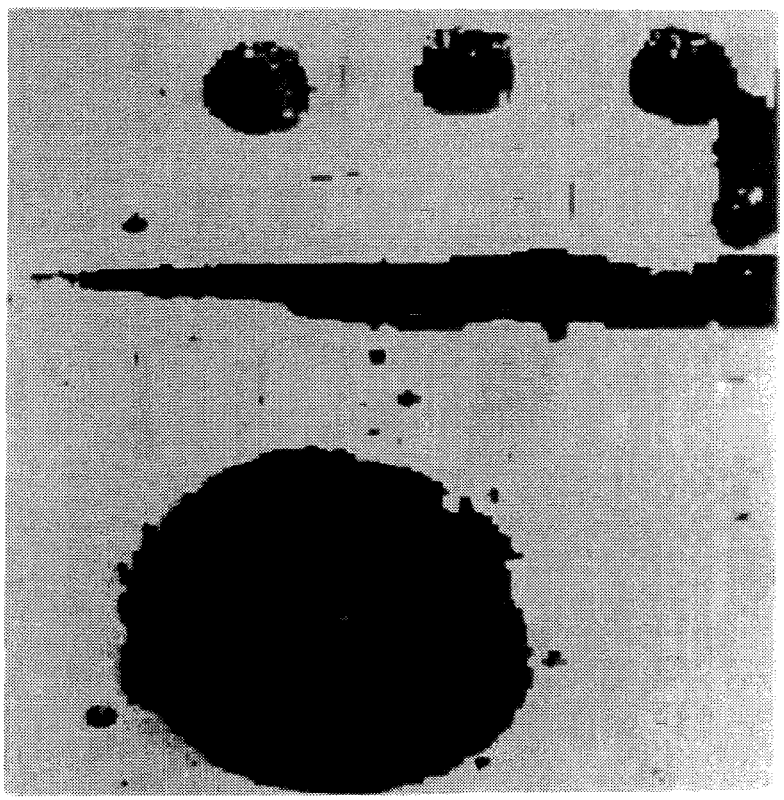
Figure 7D:
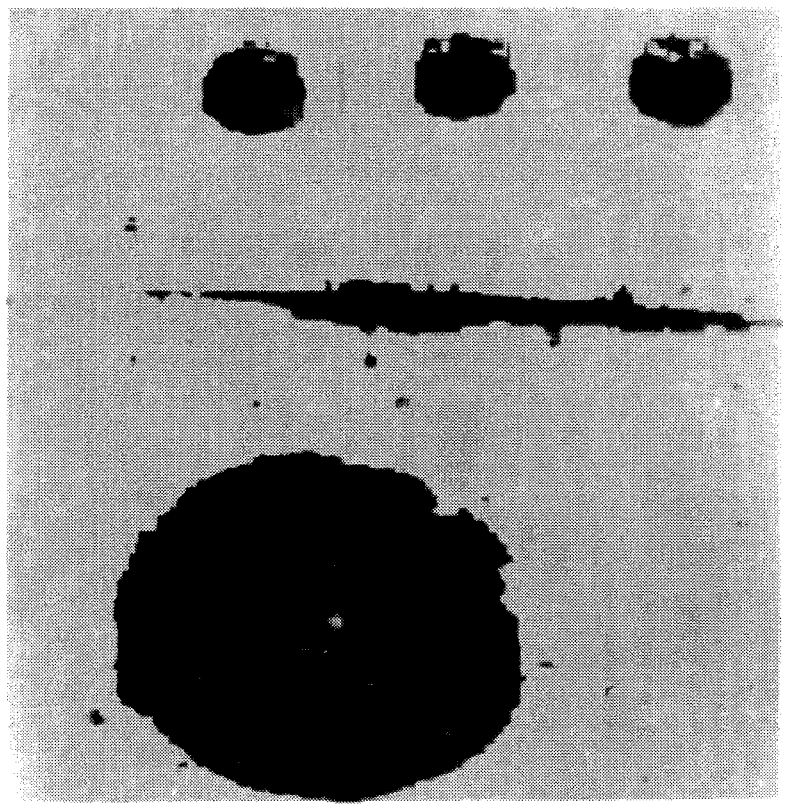
Figure 7E:
Figure 7F:
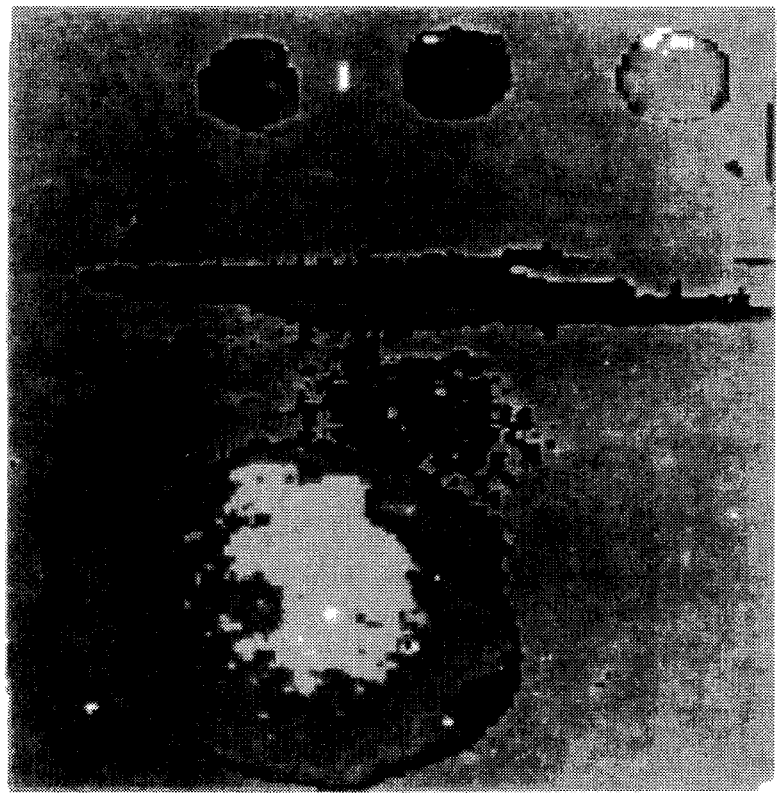
Figure 7G:
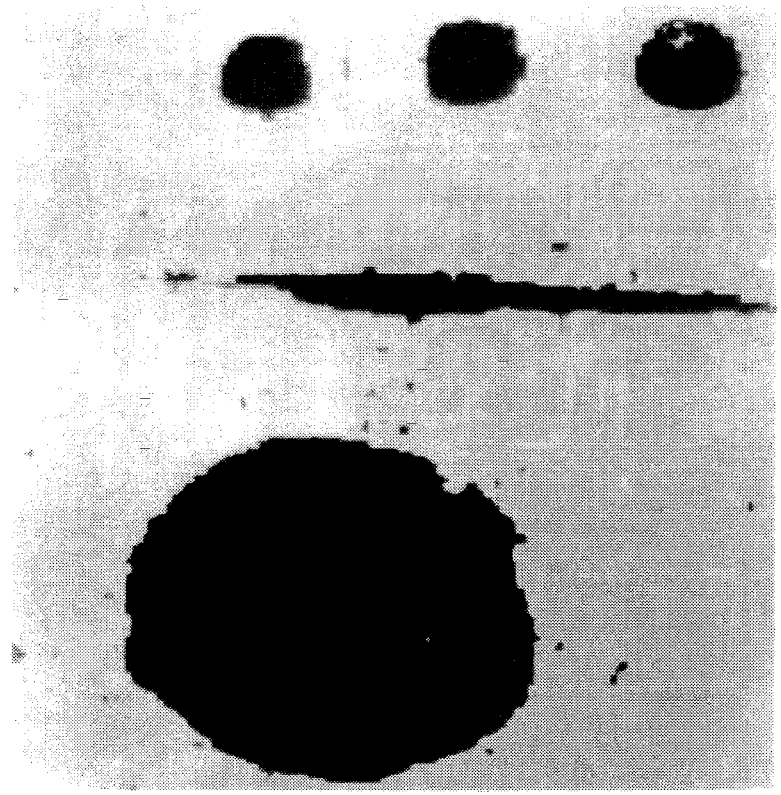

FIG. 7B is the 420 nanometer spectral image produced when the excitation illumination was 314 nanometers. Since the UV excitation energy was blocked by long pass filter 7, the only contributor to the image shown in FIG. 7B was fluorescing compounds in the sediment layer. Across the top of the image shown in FIG. 7B can be clearly seen two reference standards (nos. 2 and 4) and a portion of a third reference standard (no. 3). Near the water-sediment boundary can be seen some bright fluorescence activity, and below the water-sediment boundary can be seen a significantly bright round fluorescence activity.

Reference cell nos. 1–4 are ordered in FIGS. 7B–7G from left to right. Reference cell no. 1 of the four reference cells at the top of the imaging window contained a sediment sample substantially free of contaminants (i.e., the blank). Reference cell no. 2 contained a sediment sample spiked with 1,000 parts per million of anthracene. Reference cell no. 3 contained a sediment sample spiked with 1,000 parts per million of benzo(a)pyrene. Reference cell no. 4 contained a sediment sample spiked with 1,000 parts per million of pyrene. The large bright circle below the water-sediment interface is a fluorescent response from a test mixture containing 500 parts per million anthracene, 500 parts per million of pyrene and 500 parts per million benzo(a)pyrene.

In order to normalized the imagewise data to produce the image shown in FIG. 7B, the raw imagewise data was corrected according to the sediment sample which is substantially free of contaminants. The imagewise data represents raw intensities of the fluoroscopic emissions from contaminants in the sediment layer as detected by camera 4. In order to normalize the data to a sample free of contaminants, an intensity of the imagewise data collected by camera 4 in the area of the first reference cell was first determined. This intensity was then subtracted/added to all pixels in the uncorrected imagewise data so that the first reference cell in FIG. 7B does not "light up" because its intensity is below a preset detection limit.

This measurement process was then repeated for each of the other filters (430, 450, 470, 490 and 500 nanometers) to produce the images shown in FIGS. 7C through 7G, respectively.

A spectrum of a mix of the three "unknown" contaminants shown in FIGS. 7B through 7G was then determined. The intensity of the three unknown contaminants at each of the wavelengths represented by the images in FIGS. 7B through 7G was determined and plotted in the graph shown in FIG. 7H. The curved line in FIG. 7H was formed as a cubic spline curve fit. This is the characteristic spectrum of the three unknown contaminants. A similar process was used to determine the spectrum of each of the standard reference samples. Five spectra in all were produced, spectra 1–4 correspond to reference standards 1–4 (1 being the sediment sample substantially free of contaminants) and the fifth spectrum is the spectrum of the unknown to be identified.

Figure 7H:
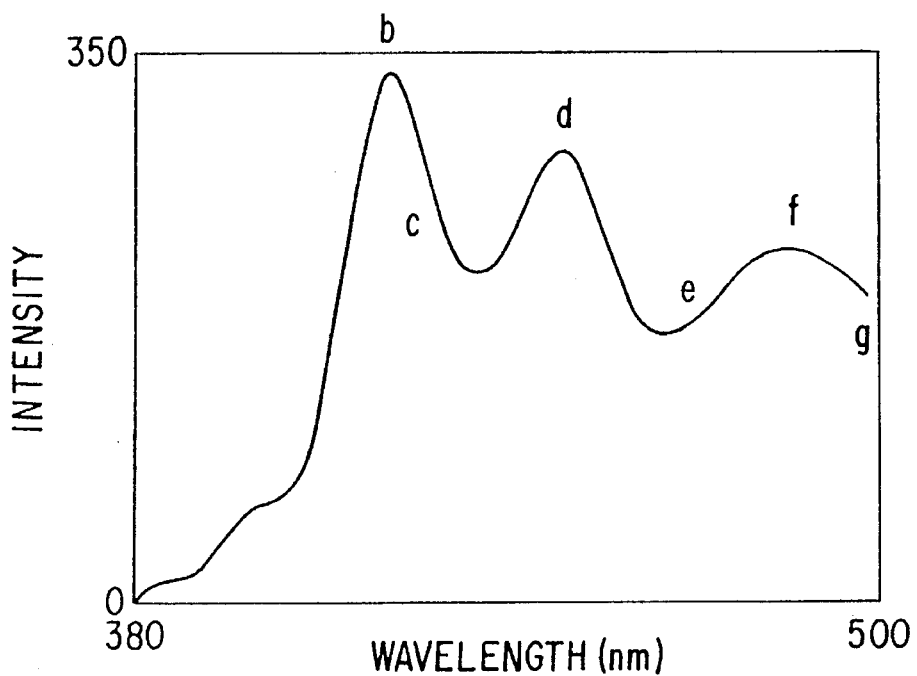
FIG. 7H is a graph showing the emission spectrum of a mixture of contaminants corresponding to the spectral images depicted in FIGS. 7B–7G.
Figure 8:
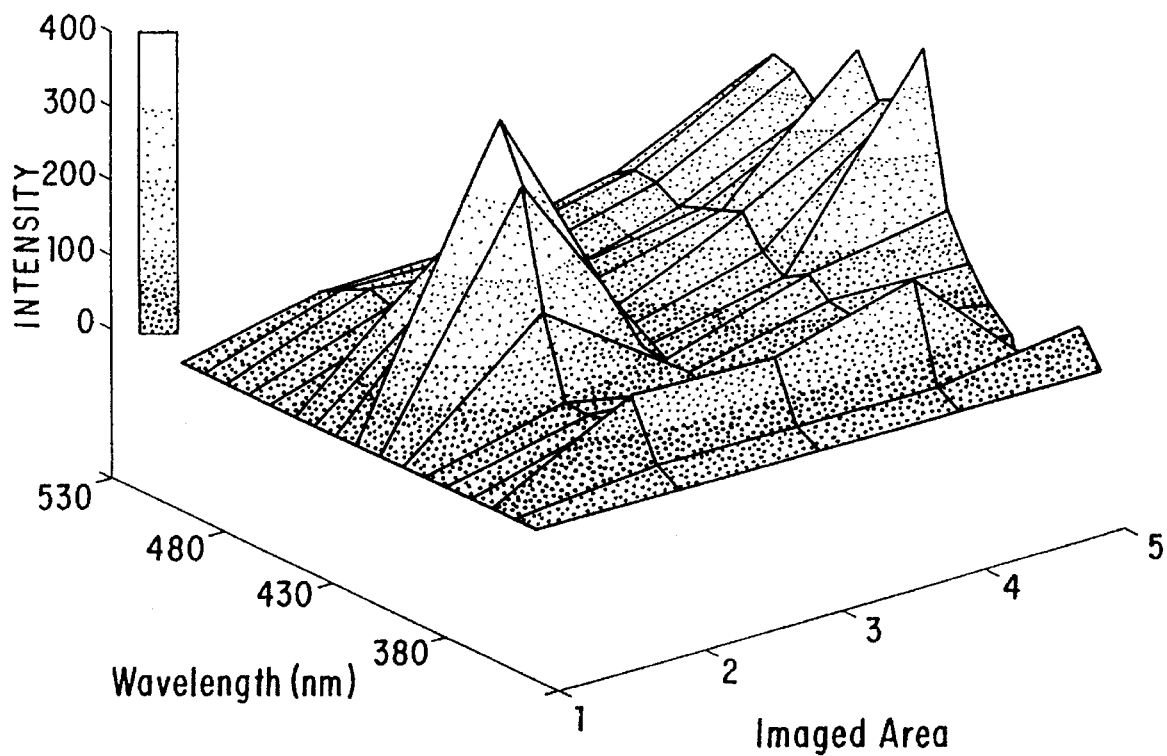
FIG. 8 is a three dimensional graph showing spectral intensity (excited from a 314 nanometer excitation wavelength source) as a function of wavelength for four standard samples and a spiked test sample (i.e., a test sample into which a known quantity of a known contaminant mix is injected).

In FIG. 8, a three-dimensional graph is shown. The vertical dimension is the intensity of the normalized spectral response. One of the horizontal dimensions reflects the wavelengths of the spectrum being plotted. The other horizontal dimension is an index to the particular spectrum being plotted. Spectrum 1 is the sediment sample substantially free of contaminants and as can be seen in FIG. 8, spectrum 1 has approximately 0 intensity. Spectrum 2 corresponds to replaceable cell 2 (spiked with 1000 parts per million of anthracene). Spectrum 3 corresponds to replaceable cell 3 (spiked with 1000 parts per million of benzo(a)pyrene). Spectrum 4 corresponds to replaceable cell 4 (spiked with 1000 parts per million of pyrene). Spectrum 5 corresponds to the mix of the three "unknown" contaminants. In this test this mix of unknown contaminants was a 1:1:1 mix of anthracene, benzo(a)pyrene and pyrene at 500 parts per million each. The intensity shown for spectrum 5 in FIG. 8 corresponds to the intensity shown in the spectrum depicted in the graph of FIG. 7H. Thus, it can be seen that the three dimensional graph shown in FIG. 8 is a powerful tool for making a qualitative identification of the unknown contaminant.

Figure 6:
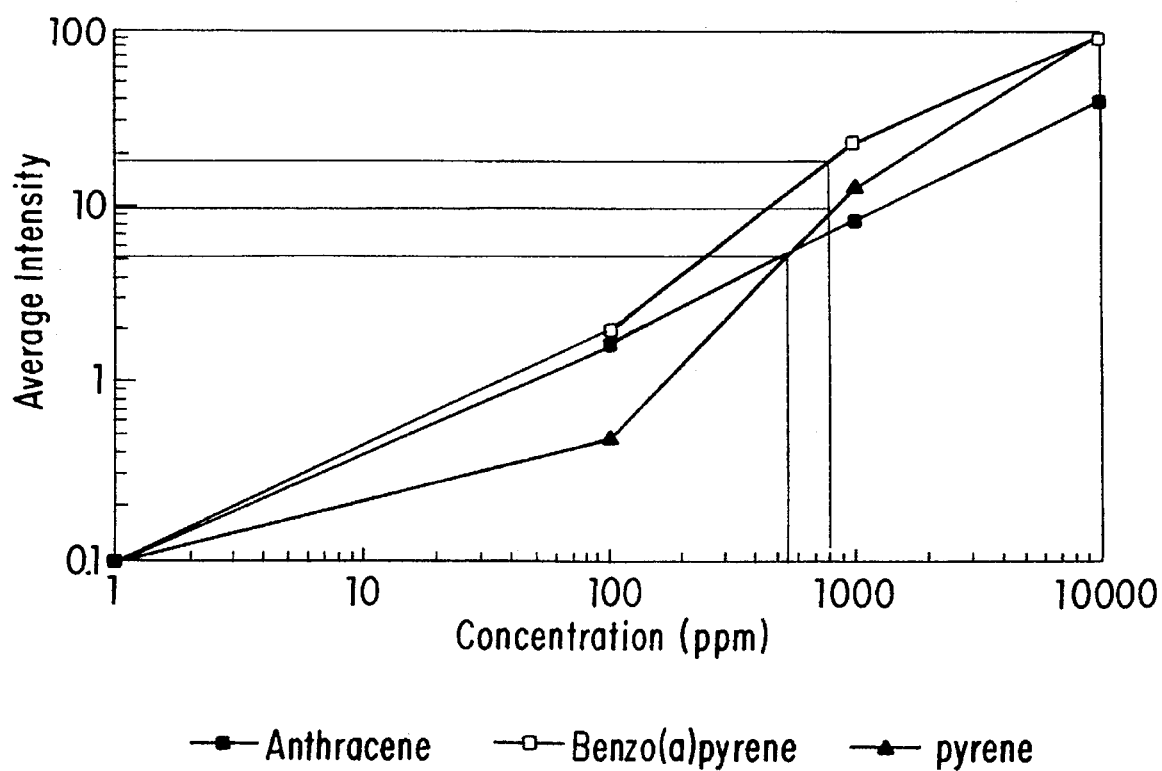
FIG. 6 is a graph showing emission as a function of concentration of imaged hydrocarbon concentrations in the sediment profile for a blank corrected one second exposure.

The spectrometer system provides a powerful tool for estimating the quantity of particular contaminants trapped in the sediment layer. The prototype was used to conduct tests of this method for estimating contaminant concentrations. In a first test, reference cells 2–4 contained sediment spiked with 100, 1000, 10,000 parts per million, respectively, of anthracene. Thereafter, the same data sets whose images are shown in FIGS. 7B through 7G, were collected. The intensities at the various emission wavelengths were averaged for each of the reference cells 2–4 and plotted in FIG. 6. In a second test, the contaminants in the referenced standards were replaced with the respective concentrations of benzo(a)pyrene, and in a third test, the contaminants in reference cells 2–4 were replaced with their respective concentrations of pyrene. All intensifies were corrected for the sediment blank in cell no. 1 and normalized to a one second exposure time. The intensity results have been plotted against their respective concentrations for each of the three polycyclic aromatic hydrocarbons in FIG. 6. An estimate of the concentration of the particular polycyclic aromatic hydrocarbon in the imaged sediment layer (below the water-sediment interface) is made by determining the intensity of the emission from the suspected contaminant area (y-axis) and projecting this intensity onto a particular curve shown in FIG. 6 to determine an intercept point and then dropping a dotted line from this intercept point to the concentration axis (x-axis). Using this method, the imaged test sediment was determined to have a polycyclic aromatic hydrocarbon concentration range of 550 to 800 parts per million (depending on the particular contaminant). The actual spiked concentrations were prepared at 500 parts per million for each polycyclic aromatic hydrocarbon.

In field deployment, because survey goals differ from project to project, the instrument may require some pre-survey preparation. First, the surveyor needs to list the compounds of interest and threshold concentrations of concern. Small representative samples of reference (low contaminant or background) sediment from the survey area may also be needed to prepare blanks and spiked standards.

Information on target compounds and threshold concentrations are entered into controller 42 that specifies optimal instrument settings for specific compound identification and quantification including: excitation/emission frequencies, spacing of emission filters, pixel binning requirements and emission read times. Once the appropriate excitation and emission filters have been installed in the filter wheels (illumination/excitation filter device 15, blocking filter device 7 and camera filter device 6 in FIG. 1), signal acquisition times for each emission wavelength entered, and appropriate blanks and spiked sediment standards have been prepared, the system is ready for deployment.

Optimal instrument settings will be based on a unique spectral library of fuel oils, crude oil, an individual polycyclic aromatic hydrocarbons, as may be developed for the instrument. The spectral library is based on spectrometer measurement of spiked sediments having a defined grain-size, mineralogy, organic carbon content and pore water salinity.

After the camera-sensor has been deployed on the seabed and the optical prism (sensor 20) has cut a vertical profile of the bottom, data collection begins. First, a red, green, blue color image is obtained followed by UV excited fluorescing emission spectra. Representative camera measurement times are one emission band within one to five seconds. To collect the data used for FIGS. 7A–7G would require 9–45 seconds (since the image shown in FIG. 7A requires a red image, a green image and a blue image).

It is desirable to maintain bottom deployment time as short as possible. With a short bottom deployment time, the sensor can be deployed from small vessels having lengths in the range of 40 to 60 feet without complicated station-keeping equipment such as thrusters. When the sensor is first deployed on the bottom, cable 32 is approximately vertical. There is deployed sufficient slack in cable 32 so that the drift of the vessel under normal conditions is insufficient to cause cable 32 to loose its slack, pull on sensor 20 and disturb the measurement process during the 45 seconds or so required to take the measurements. If the bottom measurement times are too large, the cable angles become large due to vessel drift-off and the sensor is pulled over so that the sensor's measurements are disturbed. This problem becomes worse in shallow waters. Experience with the REMOTS(tm) sensor (a sediment-profile camera first described and practiced by Rhoads and Cande, "Sediment Profile Camera For In Situ Study of Organism-Sediment Relations," *Limnology and Oceanography*, Vol 16, No. 1, pp. 110–114, 1971) over a 20 year time period in conducting marine surveys in coastal waters of the east coast of the United States teaches that the maximum available time period for conducting measurements is about 60 seconds. After the maximum available time period, there is a significant likelihood that the measurement procedure will be disturbed. Benign weather, tide and wave conditions may extend this time, but adverse weather surely shortens this time. On average, to make this type of spectrometer system economically useful for all-season marine survey applications, the maximum available time period for conducting measurements must be assumed to be about 60 seconds.

If the maximum available time period for measurement is exceeded and the sensor is tipped over due to vessel drift-off, the sensor must be redeployed at the same station (usually a 10 meter diameter circle) before the measurement process can proceed. The additional time required to reposition the vessel for acquiring replicate measurements compromises the survey efficiency.

Actual bottom times will be dictated by the fluorescence yield of the target compounds, specified concentration thresholds for detection and the number of excitation/emission channels required to identify large compounds as determined by the spectral library and pre-survey preparation protocol. Under normal circumstances (i.e., weather, currents, bottom depth, etc.) during which a survey may be undertaken, six UV images and three images for RGB color can be acquired before there is a need to reposition the sensor due to vessel drift. The sensor can acquire this data in a data collection time period less than 60 seconds, usually less than 45 seconds. This corresponds to the maximum available time period during which the sensor can be expected to remain undisturbed on the sea bottom by a drifting survey vessel. This feature permits such surveys to be conducted in all but the most adverse of weather conditions by vessels not equipped with station keeping equipment.

When the target compounds are complex and many, the specified concentration threshold for detection is low, and the fluorescence of the target compounds is weak, it becomes increasingly difficult to obtain adequate measurements in the maximum available time period for measurement. Under these circumstances, CCD camera 4 is programmably configured to collect RGB images at normal spatial resolution to observe sediment structural features (i.e., morphology), but collect fluoroscopic images at reduced spatial resolution (i.e. using enlarged virtual pixels) so that the data collection time per image may be kept small while the camera sensitivity is increased. Thus, a larger number of images may be collected in the same time period (e.g., when the number of compounds to identify is many), each individual image being collected in a shorter time period due to the increased sensitivity of the camera reconfigured to function at lower spatial resolution. Or, the same number of images may be collected in the same time period, but each image is collected with an increased sensitivity camera (e.g., when the fluorescence of the target compounds is weak) due the camera being reconfigured to function at a lower spatial resolution.

Controller 42 is a powerful development tool for collecting, storing and analyzing the image spectral while the survey is underway. Data acquisition and analysis includes three steps: (1) displaying the conventional RGB image to identify stratigraphic features of interest such as dredged material or sludge layers, or oil globules, (2) visual display of the total UV emission bands (addition of corresponding pixels in each spectra) in order to rank a replicate as falling above or below the threshold concentration of concern and (3) analyzing component compounds and their concentrations for the particular station subset falling above the pre-selected threshold concentration (hot spots). An example of such a quick-look analysis is shown in FIG. 3 at 44, 46 and 48 and in FIG. 6. At a minimum, by the end of the survey day, a map of hot spots may be prepared. The degree of quantification and compound identification depends on the number of stations/replicates and spectral complexity of the data files.

Spectral unfolding of complex mixtures, and relating this mixtures to imaged sedimentary structures, may require post-cruise analysis using processes for extracting spectra from each pixel in the imaged field of interest. For example, the triple mixed spectrum shown in FIG. 7H shows three distinct peaks. By comparing the positions of these peaks with a spectral library of the three component polycyclic aromatic hydrocarbons, one can identify the peak at Co) as being anthracene, the peak at (d) as being anthracene plus pyrene, and the broad peak at (f) as being anthracene plus benzo(a)pyrene plus pyrene. The degree of quantification and spectral analysis is determined by the survey requirements. For example, mapping of negative buoyant globules of crude oil may require less sophisticated analysis then mapping a broad mixture of polycyclic aromatic hydrocarbons bound in sediment grains. The field screening sensor described herein is a rapid field screening system for efficiently defining hot spots and monitoring the effectiveness of remediation. If required, hot spot maps can be used to identify a parsimonious subset of stations for more detailed chemical analysis using traditional methods.

Having described preferred embodiments of a novel spectrometer system (which are intended to be illustrative and not limiting), it is noted that modifications and variations can be made by those skilled in the an in light of the above teachings. It is therefore to be understood that changes may be made in the particular embodiments of the invention disclosed which are within the scope and spirit of the invention as defined by the appended claims.

Having thus described the invention with the details and particularity required by the patent laws, what is claimed and desired protected by Letters Patent is set forth in the following claims.

What is claimed is:

1. A spectrometer system comprising a processing center, an underwater remote sensor and a communications link coupled therebetween, the sensor at least partially penetrating a sediment layer disposed beneath a body of water, the sensor comprising:
   a window defining a sediment window plane through which a profile of the sediment layer is observable; and
   a CCD camera, an image plane of which is a conjugate of the window, the camera sensing light from objects in the sediment window plane as received at the camera to generate imagewise data for transmission over the communications link, the CCD camera being controllable by the processing center to generate the imagewise data so as to be formed with a selectable one of a plurality of resolutions.

2. The system of claim 1, wherein the sensor further comprises at least one removable cell disposed in the sediment window plane, each removable cell being comprised of a transparent solid material having a void therein, the void in each removable cell for holding a standard material corresponding to the respective removable cell.

3. The system of claim 1, wherein the sensor further includes a buffer unit to collect the imagewise data, the buffer unit being coupled to the transmission link.

4. The system of claim 1, wherein the camera is responsive to radiant energy within a predetermined band of wavelengths, the predetermined band of wavelengths being wavelengths in a range between 350 and 600 nanometers.

5. The system of claim 1, wherein the sediment window plane is characterized by an imageable area, the imageable area being at least as large as 300 square centimeters.

6. A spectrometer system comprising a processing center, an underwater remote sensor and a communications link coupled therebetween, the sensor at least partially penetrating a sediment layer disposed beneath a body of water, the sensor comprising:
   a window defining a sediment window plane through which a profile of the sediment layer is observable; and
   a camera, an image plane of which is a conjugate of the window, the camera sensing light from objects in the sediment window plane as received at the camera to generate imagewise data for transmission over the communications link, wherein the sensor further comprises at least one removable cell disposed in the sediment window plane, each removable cell being comprised of a transparent solid material having a void therein, the void in each removable cell for holding a standard material corresponding to the respective removable cell.

7. The system of claim 6, wherein a first removable cell includes a first standard material held in the void of the first removable cell, the first standard material comprising one of a sediment substantially free of contaminants and a sediment spiked with a known quantity of a known contaminant.

8. The system of claim 7, wherein the first standard material subtends a portion of the sediment window plane.

9. A spectrometer system comprising a processing center, an underwater remote sensor and a communications link coupled therebetween, the sensor at least partially penetrating a sediment layer disposed beneath a body of water, the sensor comprising:
   a window defining a sediment window plane through which a profile of the sediment layer is observable; and
   a camera, an image plane of which is a conjugate of the window, the camera sensing light from objects in the sediment window plane as received at the camera to generate imagewise data for transmission over the communications link, wherein the sensor further includes a camera filter device, the camera filter device including a plurality of camera filters, each camera filter being characterized as passing radiant energy within a corresponding camera band of wavelengths, the plurality of camera filters including a current camera filter, the camera filter device being controllable by the processing center to position the current camera filter between the sediment window plane and the camera so that light from the sediment window plane passes through the current camera filter before reaching the camera.

10. A spectrometer system comprising a processing center, an underwater remote sensor and a communications link coupled therebetween, the sensor at least partially penetrating a sediment layer disposed beneath a body of water, the sensor comprising:
   a window defining a sediment window plane through which a profile of the sediment layer is observable; and
   a camera, an image plane of which is a conjugate of the window, the camera sensing light from objects in the sediment window plane as received at the camera to generate imagewise data for transmission over the communications link, wherein the sensor further comprises:
   a camera filter device, the camera filter device including at least one camera filter, each camera filter being characterized as passing radiant energy within a corresponding camera band of wavelengths, the at least one camera filter including a current camera filter the camera filter device being controllable to position the current camera filter between the sediment window plane and the camera so that light from the sediment window plane passes through the current camera filter before reaching the camera;
   an illumination source; and
   at least one removable cell disposed in the sediment window plane, each removable cell being comprised of a transparent solid material having a void therein, the void in each removable cell for holding a standard material corresponding to the respective removable cell, a first removable cell including a sediment sample substantially free of contaminants held in the void of the first removable cell, the sediment layer and the sediment sample being illuminated by light from the illumination source, light from the sediment window plane including illuminated sediment layer light from the illuminated sediment layer and illuminated sediment sample light from the illuminated sediment sample, the imagewise data generated from light received at the camera after having been filtered by the current camera filter including sediment sample data corresponding to the sediment sample light.

11. The system of claim 10, wherein:

the at least one camera filter includes a red filter, a blue filter and a green filter; and the filter device includes a mechanism to alternatively position the red filter as the current camera filter, the blue filter as the current camera filter and the green filter as the current camera filter.

12. The system of claim 11, wherein the processing center includes circuitry to collect the imagewise data as red imagewise data when the red filter is the current camera filter, to collect the imagewise data as blue imagewise data when the blue filter is the current camera filter, to collect the imagewise data as green imagewise data when the green filter is the current camera filter, and to combine the red, blue and green imagewise data to produce color image data, the color image data being characterized by values representative of an intensity of light from the sediment window plane within a visible band of wavelengths, the color image data including sediment sample color data corresponding to the illuminated sediment sample light.

13. The system of claim 12, wherein the color image data includes a plurality of color image pixels, the sediment sample color data includes at least one sediment sample pixel, and the circuitry of the processing center further includes:

means for determining from the sediment sample color data an average intensity value of the at least one sediment sample pixel;

means for deducting the average intensity value from each pixel of the plurality of color image pixels to produce normalized data; and a display to display the normalized data.

14. A spectrometer system comprising a processing center, an underwater remote sensor and a communications link coupled therebetween, the sensor at least partially penetrating a sediment layer disposed beneath a body of water, the sensor comprising:

a window defining a sediment window plane through which a profile of the sediment layer is observable; and a camera, an image plane of which is a conjugate of the window, the camera sensing light from objects in the sediment window plane as received at the camera to generate imagewise data for transmission over the communications link, wherein the sensor further includes:

an illumination source to produce radiant energy; and an illumination filter device, the illumination filter device including at least one illumination filter, each illumination filter being characterized as passing radiant energy within a corresponding illumination band of wavelengths, the at least one illumination filter including a current illumination filter, the illumination filter device being controllable to position the current illumination filter in an optical path between the sediment window plane and the illumination source so that the sediment window plane is illuminated by the radiant energy from the illumination source after having been filtered by the current illumination filter.

15. The system of claim 14, wherein the sensor further includes a camera filter device, the camera filter device including at least one camera filter, each camera filter being characterized as passing radiant energy within a corresponding camera band of wavelengths, the at least one camera filter including a current camera filter, the camera filter device being controllable to position the current camera filter in an optical path between the sediment window plane and the camera so that light from the sediment window plane passes through the current camera filter before reaching the camera.

16. The system of claim 14, wherein the illumination source includes a mercury lamp.

17. A spectrometer system comprising a processing center, an underwater remote sensor and a communications link coupled therebetween, the sensor at least partially penetrating a sediment layer disposed beneath a body of water, the sensor comprising:

a window defining a sediment window plane through which a profile of the sediment layer is observable; and a camera, an image plane of which is a conjugate of the window, the camera sensing light from objects in the sediment window plane as received at the camera to generate imagewise data for transmission over the communications link, wherein the sensor further includes:

an illumination source to produce radiant energy;

an illumination filter device, the illumination filter device including at least one illumination filter, each illumination filter being characterized as passing radiant energy within a corresponding illumination band of wavelengths, the at least one illumination filter including a current illumination filter, the illumination filter device being controllable to position the current illumination filter in an optical path between the sediment window plane and the illumination source so that the sediment window plane is illuminated by the radiant energy from the illumination source after having been filtered by the current illumination filter; and a blocking filter device, the blocking filter device including at least one blocking filter, each blocking filter being characterized as blocking radiant energy within a corresponding blocking band of wavelengths, the at least one blocking filter including a current blocking filter, the blocking filter device being controllable to position the current blocking filter in an optical path between the sediment window plane and the camera so that light from the sediment window plane passes through the current blocking filter before reaching the camera, the blocking filter device being controlled to select the current blocking filter synchronously with the current illumination filter so that the radiant energy which passes through the current illumination filter is blocked from reaching the camera by the current blocking filter.

18. A spectrometer system comprising a processing center, an underwater remote sensor and a communications link coupled therebetween, the sensor at least partially penetrating a sediment layer disposed beneath a body of water, the sensor comprising;

a window defining a sediment window plane through which a profile of the sediment layer is observable; and a camera, an image plane of which is a conjugate of the window, the camera sensing light from objects in the sediment window plane as received at the camera to generate imagewise data for transmission over the communications link, wherein the sensor further comprises a plurality of removable cells disposed in the sediment window plane, each removable cell being comprised of a transparent solid material having a void therein, the void in each removable cell for holding a standard material corresponding to the respective removable cell, the plurality of removable cells including a first removable cell and a second removable cell, the first removable cell holding a first standard sediment sample held in the void of the first removable cell, the second removable cell holding a second standard sediment sample held in the void of the second removable cell, the first standard sediment sample comprising a first known quantity of a known contaminant, the second standard sediment sample comprising a second known quantity of the known contaminant, the second quantity being greater than the first quantity.

19. The system of claim 18, wherein the sensor further includes a camera filter device, the camera filter device including at least one camera filter, each camera filter being characterized as passing radiant energy within a corresponding camera band of wavelengths, the at least one camera filter including a current camera filter, the camera filter device being controllable to position the current camera filter between the sediment window plane and the camera so that light from the sediment window plane passes through the current camera filter before reaching the camera.

20. The system of claim 19, wherein the sensor further includes:

an illumination source to produce radiant energy; and an illumination filter device, the illumination filter device including at least one illumination filter, each illumination filter being characterized as passing radiant energy within a corresponding illumination band of wavelengths, the at least one illumination filter including a current illumination filter, the illumination filter device being controllable to position the current illumination filter in an optical path between the sediment window plane and the illumination source so that the sediment window plane is illuminated by the radiant energy from the illumination source after having been filtered by the current illumination filter.

21. The system of claim 20, wherein the illumination filter device is controlled to select a first illumination filter as the current illumination filter, the first illumination filter is characterized as passing radiant energy within a first illumination band of the at least one illumination band, the camera filter device is controlled to select a first camera filter as the current camera filter, the first camera filter is characterized as passing radiant energy within a first camera band of the at least one camera band, at least a portion of the sediment layer and of the first and second standard sediment samples fluoresces to emit light from within the sediment window plane in response to radiant energy within the first illumination band, the first camera band is different than the first illumination band, light from the sediment window plane includes first sediment sample light from the illuminated first standard sediment sample and second sediment sample light from the illuminated second standard sediment sample, the imagewise data includes first and second sediment sample data corresponding to the first and second sediment sample light, and the processing center comprises:

means for determining a first standard intensity corresponding to the first quantity of the known contaminant from the first sediment sample data of the normalized data;

means for determining a second standard intensity corresponding to the second quantity of the known contaminant from the second sediment sample data of the normalized data;

means for displaying the normalized data;

means for determining a suspected contaminant intensity corresponding to a suspected contaminant area displayed within the displayed normalized data, the suspected contaminant area being defined by a user; and means for determining an estimate of a quantity of the known contaminant contained in the suspected contaminant area from the suspected contaminant intensity and the first and second standard intensities.

22. A spectrometer system comprising a processing center, an underwater remote sensor and a communications link coupled therebetween, the sensor at least partially penetrating a sediment layer disposed beneath a body of water, the sensor comprising:

a window defining a sediment window plane through which a profile of the sediment layer is observable; and a camera, an image plane of which is a conjugate of the window, the camera sensing light from objects in the sediment window plane as received at the camera to generate imagewise data for transmission over the communications link, wherein the sensor further comprises at least one removable cell disposed in the sediment window plane, each removable cell being comprised of a transparent solid material having a void therein, the void in each removable cell for holding a standard material corresponding to the respective removable cell, a first removable cell holding a sediment sample substantially free of contaminants in the void of the first removable cell.

23. The system of claim 22, wherein the sensor further includes:

an illumination source to produce radiant energy; and an illumination filter device, the illumination filter device including at least one illumination filter, each illumination filter being characterized as passing radiant energy within a corresponding illumination band of wavelengths, the at least one illumination filter including a current illumination filter, the illumination filter device being controllable to position the current illumination filter in an optical path between the sediment window plane and the illumination source so that the sediment window plane is illuminated by the radiant energy from the illumination source after having been filtered by the current illumination filter.

24. The system of claim 23, wherein the sensor further includes a camera filter device, the camera filter device including at least one camera filter, each camera filter being characterized as passing radiant energy within a corresponding camera band of wavelengths, the at least one camera filter including a current camera filter, the camera filter device being controllable to position the current camera filter between the sediment window plane and the camera so that light from the sediment window plane passes through the current camera filter before reaching the camera.

25. The system of claim 24, wherein the illumination filter device is controlled to select a first illumination filter as the current illumination filter, the first illumination filter is characterized as passing radiant energy within a first illumination band, at least a portion of the sediment layer and the sediment sample fluoresces to emit light from within the sediment window plane in response to radiant energy within the first illumination band, light from the sediment window plane includes sediment sample light from the illuminated sediment sample, the imagewise data includes sediment sample data corresponding to the sediment sample light, the at least one camera filter includes a plurality of camera filters and the processing center comprises:

repeater control to successively select a selected camera filter of the plurality of camera filters as the current camera filter, the imagewise data generated by the camera for each selected camera filter of the plurality of camera filters constituting a respective plurality of data sets; and means for normalizing each data set of the plurality of data sets based on the sediment sample data to produce a plurality of normalized data sets.

26. The system of claim 25, wherein the plurality of normalized data sets includes a first normalized data set and at least one more normalized data set, the processing center further including:

a display to display the first normalized data set;

means for determining a first suspected contaminant intensity pertaining to a suspected contaminant area displayed within the displayed first normalized data set, the suspected contaminant area being defined by a user; and means for determining at least one more suspected contaminant intensity pertaining to the suspected contaminant area in each of the respective at least one more normalized data set, the first suspected contaminant intensity and the at least one more suspected contaminant intensity constituting a plurality of suspected contaminant intensities, each intensity of the plurality of suspected contaminant intensities corresponding to a respective camera filter characterized by a corresponding filter band, the plurality of suspected contaminant intensities together with corresponding filter bands constituting a suspected contaminant spectrum.

27. The system of claim 26, wherein the processing center further comprises means for identifying a suspected contaminant from the suspected contaminant spectrum.

28. A spectrometer system comprising a processing center, an underwater remote sensor and a communications link coupled therebetween, the sensor at least partially penetrating a sediment layer disposed beneath a body of water, the sensor comprising:

a window defining a sediment window plane through which a profile of the sediment layer is observable; and a camera, an image plane of which is a conjugate of the window, the camera sensing light from objects in the sediment window plane as received at the camera to generate imagewise data for transmission over the communications link, wherein:

the sediment layer defines at least one stratigraphic feature, the at least one stratigraphic feature including a first stratigraphic feature, the first stratigraphic feature subtending a stratigraphic feature area; and the sediment window plane is characterized by an imageable area, the imageable area being larger than the stratigraphic feature area and being at least 300 square centimeters.

29. The system of claim 28, wherein the first stratigraphic feature includes a precipitate layer of negative buoyancy oil particles which precipitate out of the body of water onto the sediment layer.

30. A spectrometer system comprising a processing center, an underwater remote sensor and a communications link coupled therebetween, the sensor at least partially penetrating a sediment layer disposed beneath a body of water, the processing center controlling the sensor to collect color image data and processing the collected color image data to determine an apparent reduction/oxidation potential of a part of the sediment layer.

31. The system of claim 30, wherein the system determines the apparent reduction/oxidation potential between −200 millivolts and +200 millivolts.

32. A spectrometer system comprising a processing center, an underwater remote sensor and a communications link coupled therebetween, the sensor at least partially penetrating a sediment layer disposed beneath a body of water, the processing center controlling the sensor to collect data and processing the collected data to determine a spectrum of fluorescence of a compound contained in the sediment layer.

33. The system of claim 32, wherein the processing center further processes the collected data to identify a species of the compound.

34. A spectrometer system comprising a processing center, an underwater remote sensor and a communications link coupled therebetween, the sensor at least partially penetrating a sediment layer disposed beneath a body of water, the processing center controlling the sensor to collect data and processing the collected data to determine a concentration of a compound contained in the sediment layer.

35. The system of claim 34, wherein the processing center further processes the collected data to determine a spectrum of fluorescence of the compound.

36. The system of claim 35, wherein the processing center further processes the collected data to identify a species of the compound.

37. A spectrometer system comprising a processing center, an underwater remote sensor and a communications link coupled therebetween, the sensor at least partially penetrating a sediment layer disposed beneath a body of water, the processing center controlling the sensor to collect data and processing the collected data to identify a species of a compound contained in the sediment layer.

38. A spectrometer system comprising a processing center on a vessel without station-keeping equipment, an underwater remote sensor and a communications link coupled therebetween, the sensor having been deployed to at least partially penetrate a sediment layer disposed beneath a body of water, the processing center controlling the sensor to collect a plurality of sets of imagewise data within a data collection time period, a maximum available time period being defined as a time period beginning when data collection of a first set of imagewise data begins and ending when the sensor penetration into the sediment layer is disturbed due to drifting of the vessel, the data collection time period being less than the maximum available time period.

39. The system of claim 38, wherein the plurality of sets of imagewise data collected during the data collection time period includes nine data sets of imagewise data.

40. The system of claim 39, wherein the maximum available time period is 60 seconds.

41. The system of claim 39, wherein:

a first set of imagewise data is characterized by a first spatial resolution; and a second set of imagewise data is characterized by a second spatial resolution, the first spatial resolution being greater than the second spatial resolution.

42. The system of claim 38, wherein:
  a first set of imagewise data is characterized by a first spatial resolution; and
  a second set of imagewise data is characterized by a second spatial resolution, the first spatial resolution being greater than the second spatial resolution.

43. The system of claim 38, wherein the maximum available time period is 60 seconds.

44. The system of clam 43, wherein the plurality of sets of imagewise data collected during the data collection time period is processed by the processing center to determine characteristics of a compound contained in the sediment layer, the characteristics including at least one of a spectrum of fluorescence of the compound, an identity of a species of the compound and a concentration of the compound.

45. In a spectrometer system comprising a processing center, an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window, the camera being capable of imaging light from objects in the sediment window plane, a method of analyzing the sediment layer comprising steps of:
  illuminating the sediment layer;
  generating imagewise data corresponding to light received at the camera from the sediment window plane;
  controlling the step of generating so that the imagewise data is formed with a selectable one of a plurality of resolutions; and
  processing and displaying the imagewise data on a display.

46. The method of claim 40, wherein the step of generating includes:
  filtering light from the sediment window plane through a current camera filter of a camera filter device to provide the light received at the camera, the camera filter device having a plurality of camera filters, each camera filter passing light to the camera characterized as radiant energy within a corresponding camera band of a plurality of predetermined camera bands; and
  disposing at least one removable cell in the sediment window plane, each removable cell being comprised of a transparent solid material having a void therein for holding a respective standard material, a first removable cell including a sediment sample substantially free of contaminants held in the void of the first removable cell, the sediment layer and the sediment sample being illuminated by light from an illumination source, light from the sediment window plane including illuminated sediment layer light from the illuminated sediment layer and illuminated sediment sample light from the illuminated sediment sample, the imagewise data generated from light passing through the current camera filter including sediment sample data corresponding to the sediment sample light.

47. The method of claim 45, wherein:
  the step of illuminating includes a first step of filtering light from an illumination source through an illumination filter device having at least one illumination filter to provide radiant energy within at least one corresponding illumination band of wavelengths, at least a portion of the sediment layer fluorescing to emit light from within the sediment window plane in response to radiant energy within a first illumination band; and
  the step of generating includes a second step of filtering light from the sediment window plane through a camera filter device having at least one camera filter to pass light to the camera, the light passed to the camera being characterized as radiant energy within at least one corresponding camera band of wavelengths, a first camera band being different than the first illumination band.

48. The method of claim 45, wherein the step of illuminating includes filtering light from an illumination source to provide radiant energy within at least one predetermined illumination band of wavelengths.

49. In a spectrometer system comprising a processing center, an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window, the camera being capable of imaging light from objects in the sediment window plane, a method of analyzing the sediment layer comprising steps of:
  illuminating the sediment layer;
  generating imagewise data corresponding to light received at the camera from the sediment window plane, the step of generating including a step of filtering light from the sediment window plane to provide light received at the camera the filtered light being characterized as radiant energy within at least one predetermined camera band of wavelengths; and
  displaying the imagewise data on a display, wherein:
    the step of filtering includes filtering light from the sediment window plane through a camera filter device to provide the light received at the camera, the camera filter device having at least one camera filter, each camera filter passing light to the camera characterized as radiant energy within a corresponding camera band of the at least one predetermined camera band; and
    the step of generating further includes a step of disposing at least one removable cell in the sediment window plane, each removable cell being comprised of a transparent solid material having a void therein for holding a respective standard material, a first removable cell including a sediment sample substantially free of contaminants held in the void of the first removable cell, the sediment layer and the sediment sample being illuminated by light from an illumination source, light from the sediment window plane including illuminated sediment layer light from the illuminated sediment layer and illuminated sediment sample light from the illuminated sediment sample, imagewise data generated from light passing through a current camera filter of the at least one camera filter including sediment sample data corresponding to the sediment sample light.

50. The method of claim 49, further comprising a step of repeating the step of generating so as to affect a plurality of generating steps, the at least one camera filter including a plurality of camera filters, each generating step of the plurality of generating steps including a corresponding step of filtering, each corresponding step of filtering controlling the camera filter device to filter light from the sediment window plane through a respective camera filter of the plurality of camera filters.

51. The method of claim 50, wherein:
  a first step of filtering of the repeated steps of filtering includes filtering light from the sediment window plane through a red band filter;

a second step of filtering of the repeated steps of filtering includes filtering light from the sediment window plane through a blue band filter; and a third step of filtering of the repeated steps of filtering includes filtering light from the sediment window plane through a green band filter.

52. The method of claim 51, wherein the step of displaying includes steps of:

collecting red imagewise data while the first step of filtering filters light from the sediment window plane through the red band filter, the red image wig data being characterized by values representative of an intensity of light received at the camera through the red band filter;

collecting blue imagewise data while the second step of filtering filters light from the sediment window plane through the blue band filter, the blue imagewise data being characterized by values representative of an intensity of light received at the camera through the blue band filter;

collecting green imagewise data while the third step of filtering filters light from the sediment window plane through the green band filter, the green imagewise data being characterized by values representative of an intensity of light received at the camera through the green band filter; and combining the red, blue and green imagewise data to produce color image data, the color image data being characterized by values representative of an intensity of light from the sediment window plane within a visible band of wavelengths, the color image data including sediment sample color data corresponding to the sediment sample light characterized as radiant energy within the visible band of wavelengths.

53. The method of claim 52, wherein the color image data includes a plurality of color image pixels, the sediment sample color data includes at least one sediment sample pixel, and the step of displaying includes:

determining from the sediment sample color data an average intensity value of the at least one sediment sample pixel;

deducting the average intensity value from each pixel of the plurality of color image pixels to produce normalized data; and displaying the normalized data.

54. In a spectrometer system comprising a processing center, an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window, the camera being capable of imaging light from objects in the sediment window plane, a method of analyzing the sediment layer comprising steps of:

illuminating the sediment layer, the step of illuminating including a first step of filtering light from an illumination source through an illumination filter device, the illumination filter device having at least one illumination filter to provide radiant energy within at least one corresponding illumination band of wavelengths, at least a portion of the sediment layer fluorescing to emit light from within the sediment Window plane in response to radiant energy within a first illumination band;

generating imagewise data corresponding to light received at the camera from the sediment window plane, the step of generating including a second step of filtering light from the sediment window plane through a camera filter device having at least one camera filter to pass light to the camera, the light passed to the camera being characterized as radiant energy within at least one corresponding camera band of wavelengths, a first camera band being different than the first illumination band; and displaying the imagewise data on a display, wherein:

the step of illuminating includes controlling the illumination filter device to select a first illumination filter to pass radiant energy in the first illumination band;

the step of generating further includes a step of disposing a plurality of removable cells in the sediment window plane, each removable cell being comprised of a transparent solid material having a void therein for holding a respective standard material, a first removable cell including a first standard sediment sample held in the void of the first removable cell, the first standard sediment sample including a first known quantity of a known contaminant, a second removable cell including a second standard sediment sample held in the void of the second removable cell, the second standard sediment sample including a second known quantity of the known contaminant, the second quantity being greater than the first quantity, the first and second standard sediment samples being illuminated by the filtered light from the illumination source, light from the sediment window plane including first sediment sample light from the illuminated first standard sediment sample and second sediment sample light from the illuminated second standard sediment sample, the imagewise data including first and second sediment sample data corresponding to the first and second sediment sample light; and the method further comprising a step of normalizing the imagewise data based on a sediment sample substantially free of contaminants to produce normalized data.

55. The method of claim 54, wherein the step of displaying includes steps of:

determining a first standard intensity corresponding to the first quantity of the known contaminant from the first sediment sample data of the normalized data;

determining a second standard intensity corresponding to the second quantity of the known contaminant from the second sediment sample data of the normalized data;

displaying the normalized data;

determining a suspected contaminant intensity corresponding to a suspected contaminant area displayed within the displayed normalized data, the suspected contaminant area being defined by a user; and determining an estimate of a quantity of the known contaminant contained in the suspected contaminate area from the suspected contaminant intensity and the first and second standard intensities.

56. In a spectrometer system comprising a processing center, an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window, the camera being capable of imaging light from objects in the sediment window plane, a method of analyzing the sediment layer comprising steps of:

illuminating the sediment layer, the step of illuminating including a first step of filtering light from an illumination source through an illumination filter device, the illumination filter device having at least one illumination filter to provide radiant energy within at least one corresponding illumination band of wavelengths, at least a portion of the sediment layer fluorescing to emit light from within the sediment window plane in response to radiant energy within a first illumination band;

generating imagewise data corresponding to light received at the camera from the sediment window plane, the step of generating including a second step of filtering light from the sediment window plane through a camera filter device to pass light to the camera, the camera filter device having at least one camera filter, the light passed to the camera being characterized as radiant energy within a first camera band of wavelengths corresponding to a respective camera filter, the first camera band being different than the first illumination band; and displaying the imagewise data on a display, wherein:

the step of illuminating further includes controlling the illumination filter device to select a first illumination filter to pass radiant energy in the first illumination band;

the method further comprises a first step of repeating the step of generating so as to affect a first plurality of generating steps while the illumination filter device is controlled to select the first illumination filter, the at least one camera filter including a plurality of camera filters, each generating step of the first plurality of generating steps including a corresponding step of filtering, each corresponding step of filtering controlling the camera filter device to filter light from the sediment window plane through a respective camera filter of the plurality of camera filters;

the imagewise data generated by each generating step of the first plurality of generating steps constitutes a data set, the first plurality of generating steps generating a corresponding first plurality of data sets; and the step of displaying includes normalizing each data set of the first plurality of data sets based on a sediment sample substantially free of contaminants to produce a first plurality of normalized data sets, each data set corresponding to light passed through a corresponding camera filter.

57. The method of claim 56, wherein the first plurality of normalized data sets includes a first normalized data set and at least one more normalized data set, the step of displaying further including steps of:

displaying the first normalized data set;

determining a first suspected contaminant intensity corresponding to a suspected contaminant area displayed within the displayed first normalized data set, the suspected contaminant area being defined by a user;

determining at least one more suspected contaminant intensity corresponding to the suspected contaminant area in each of the respective at least one more normalized data set, the first suspected contaminant intensity and the at least one more suspected contaminant intensity constituting a first plurality of suspected contaminant intensities, each intensity of the first plurality of suspected contaminant intensities corresponding to a respective camera filter characterized by a corresponding filter band, the first plurality of suspected contaminant intensities together with corresponding filter bands constituting a first suspected contaminant spectrum of the first illumination band.

58. The method of claim 57, further comprising a step of identifying a suspected contaminant corresponding to the first suspected contaminant spectrum.

59. The method of claim 57, wherein:

the step of illuminating further includes controlling the illumination filter device to select a second illumination filter to pass radiant energy in a second illumination band, at least a portion of the sediment layer fluorescing to emit light from within the sediment window plane in response to radiant energy in the second illumination band;

the method further comprises a second step of repeating the step of generating so as to affect a second plurality of generating steps while the illumination filter device is controlled to select the second illumination filter, each generating step of the second plurality of generating steps including a corresponding step of filtering, each corresponding step of filtering controlling the camera filter device to filter light from the sediment window plane through a respective camera filter of the plurality of camera filters;

the imagewise data generated by each generating step of the second plurality of generating steps constitutes a data set, the second plurality of generating steps generating a corresponding second plurality of data sets; and the step of displaying further includes normalizing each data set of the second plurality of data sets based on the sediment sample to produce a second plurality of normalized data sets, each data set corresponding to light passed through a corresponding camera filter.

60. The method of claim 59, wherein the second plurality of normalized data sets includes a first normalized data set and at least one more normalized data set, the step of displaying further including a step of determining a second plurality of suspected contaminant intensities corresponding to the suspected contaminant area in each of the respective second plurality of normalized data sets, each intensity of the second plurality of suspected contaminant intensities corresponding to a respective camera filter characterized by a corresponding filter band, the second plurality of suspected contaminant intensities together with the corresponding filter bands constituting a second suspected contaminant spectrum of the second illumination band.

61. The method of claim 60, further comprising a step of identifying a suspected contaminant corresponding to the first and second suspected contaminant spectra.

62. In a spectrometer system comprising a processing center, an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window, the camera being capable of imaging light from objects in the sediment window plane, a method of analyzing the sediment layer comprising steps of:

illuminating the sediment layer, the step of illuminating including a first step of filtering light from an illumination source through an illumination filter device, the illumination filter device having at least one illumination filter to provide radiant energy within at least one corresponding illumination band of wavelengths, at least a portion of the sediment layer fluorescing to emit light from within the sediment window plane in response to radiant energy within a first illumination band;

excluding radiant energy within the first illumination band from the camera;

generating imagewise data corresponding to light received at the camera from the sediment window plane, the step of generating including a second step of filtering light from the sediment window plane through a camera filter device, the camera filter device having at least one camera filter to pass light to the camera, the light passed to the camera being characterized as radiant energy within at least one corresponding camera band of wavelengths, a first camera band being different than the first illumination band; and displaying the imagewise data on a display.

63. In a spectrometer system comprising a processing center, an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window, the camera being capable of imaging light from objects in the sediment window plane, a method of analyzing the sediment layer comprising steps of:

illuminating the sediment layer, the step of illuminating including filtering light from an illumination source to provide radiant energy within at least one predetermined illumination band of wavelengths;

generating imagewise data corresponding to light received at the camera from the sediment window plane; and displaying the imagewise data on a display, wherein the step of generating includes filtering light from the sediment window plane to block radiant energy within a first illumination band and to pass other light to the camera, the filtered light being characterized as radiant energy within at least one predetermined camera band of wavelengths.

64. In a spectrometer system comprising a processing center an underwater remote sensor and a communications link coupled therebetween, the sensor at least partially penetrating a sediment layer disposed beneath a body of water, the sensor including a window defining a sediment window plane through which a profile of the sediment layer is observable and a camera, an image plane of which is a conjugate of the window the camera being capable of imaging light from objects in the sediment window plane, a method of analyzing the sediment layer comprising steps of;

illuminating the sediment layer:

generating imagewise data corresponding to light received at the camera from the sediment window plane; and displaying the imagewise data on a display, wherein the step of generating includes disposing at least one removable cell within the sediment window plane, each removable cell being comprised of a transparent solid material having a void therein for holding a respective standard material.

65. In a spectrometer system having a processing center and a communications link, an underwater remote sensor comprising:

a window defining a sediment window plane through which a profile of a sediment layer is observable; and a CCD camera, an image plane of which is a conjugate of the window, the camera sensing light from the sediment window plane as received at the camera to generate imagewise data for transmission over the communications link, the sensor having been deployed to at least partially penetrate the sediment layer disposed beneath a body of water, the CCD camera being controllable by the processing center to generate the imagewise data so as to be formed with a selectable one of a plurality of resolutions.

66. In a spectrometer system having a processing center and a communications link, an underwater remote sensor comprising:

a window defining a sediment window plane through which a profile of a sediment layer is observable; and a camera, an image plane of which is a conjugate of the window, the camera sensing light from the sediment window plane as received at the camera to generate imagewise data for transmission over the communications link, the sensor having been deployed to at least partially penetrate the sediment layer disposed beneath a body of water, wherein the sensor further comprises at least one removable cell disposed in the sediment window plane, each removable cell being comprised of a transparent solid material having a void therein, the void in each removable cell for holding a standard material corresponding to the respective removable cell.

67. In a spectrometer system having a processing center and a communications link, an underwater remote sensor comprising:

a window defining a sediment window plane through which a profile of a sediment layer is observable; and a camera, an image plane of which is a conjugate of the window, the camera sensing light from the sediment window plane as received at the camera to generate imagewise data for transmission over the communications link, the sensor having been deployed to at least partially penetrate the sediment layer disposed beneath a body of water, wherein the sensor further includes a camera filter device, the camera filter device including a plurality of camera filters, each camera filter being characterized as passing radiant energy within a corresponding camera band of wavelengths, the plurality of camera filters including a current camera filter, the camera filter device being controllable by the processing center to position the current camera filter between the sediment window plane and the camera so that light from the sediment window plane passes through the current camera filter before reaching the camera.

68. In a spectrometer system having a processing center and a communications link, an underwater remote sensor comprising:

a window defining a sediment window plane through which a profile of a sediment layer is observable; and a camera, an image plane of which is a conjugate of the window, the camera sensing light from the sediment window plane as received at the camera to generate imagewise data for transmission over the communications link, the sensor having been deployed to at least partially penetrate the sediment layer disposed beneath a body of water, wherein the sensor further includes:

an illumination source to produce radiant energy; and an illumination filter device, the illumination filter device including at least one illumination filter, each illumination filter being characterized as passing radiant energy within a corresponding illumination band of wavelengths, the at least one illumination filter including a current illumination filter, the illumination filter device being controllable to position the current illumination filter in an optical path between the sediment window plane and the illumination source so that the sediment window plane is illuminated by the radiant energy from the illumination source after having been filtered by the current illumination filter.

* * * * *